(12) United States Patent
De Heer et al.

(10) Patent No.: US 10,716,701 B2
(45) Date of Patent: Jul. 21, 2020

(54) ORAL AND NASAL DEVICES FOR THE TREATMENT OF SLEEP APNEA AND/OR SNORING WITH FILTER AND SENSORS TO PROVIDE REMOTE DIGITAL MONITORING AND REMOTE DATA ANALYSIS

(71) Applicant: ALLREST TECHNOLOGIES, Palo Alto, CA (US)

(72) Inventors: Robert S De Heer, Palo Alto, CA (US); Jerome Hester, Palo Alto, CA (US); Juan Ramon Zarco, Palo Alto, CA (US)

(73) Assignee: ALLREST TECHNOLOGIES, Palo Alto, CA (US)

( * ) Notice: Subject to any disclaimer, the term of this patent is extended or adjusted under 35 U.S.C. 154(b) by 339 days.

(21) Appl. No.: 15/517,900

(22) PCT Filed: Oct. 7, 2015

(86) PCT No.: PCT/US2015/054559
§ 371 (c)(1),
(2) Date: Apr. 7, 2017

(87) PCT Pub. No.: WO2016/057719
PCT Pub. Date: Apr. 14, 2016

(65) Prior Publication Data
US 2017/0312118 A1 Nov. 2, 2017

Related U.S. Application Data

(60) Provisional application No. 62/060,956, filed on Oct. 7, 2014.

(51) Int. Cl.
*A62B 23/02* (2006.01)
*A61F 5/56* (2006.01)
(Continued)

(52) U.S. Cl.
CPC ............ *A61F 5/566* (2013.01); *A61B 5/4818* (2013.01); *A61B 5/4836* (2013.01); *A61F 5/08* (2013.01);
(Continued)

(58) Field of Classification Search
CPC ... A61B 1/24; A61B 17/0218; A61B 17/3423; A61B 5/01; A61B 5/0833; A61B 5/0836; A61B 5/097; A61B 90/30; A61C 5/90; A61C 7/00; A61F 5/56; A61F 5/566; A61M 15/08; A61M 15/085; A61M 16/0493;
(Continued)

(56) References Cited

U.S. PATENT DOCUMENTS 5,386,825 A * 2/1995 Bates .................. A62B 23/06
128/204.13
5,771,885 A * 6/1998 Putrello .................. A62B 7/10
128/205.27

(Continued)

*Primary Examiner* — Annette Dixon
(74) *Attorney, Agent, or Firm* — Hogan Lovells US LLP

(57) ABSTRACT

The invention relates to devices and methods for monitoring, diagnosing and/or treating sleep apnea. Devices of the invention comprise a mouthpiece having a filter assembly and a microchip. Devices of the invention may also comprise a nasal splint having a filter assembly and a microchip. The invention also relates to a system comprising devices of the invention.

11 Claims, 20 Drawing Sheets

(51) Int. Cl.
  *A61B 5/00* (2006.01)
  *A61F 5/08* (2006.01)
  *A62B 23/06* (2006.01)

(52) U.S. Cl.
  CPC ................ *A61F 5/56* (2013.01); *A62B 23/02* (2013.01); *A62B 23/06* (2013.01); *A61B 2560/0214* (2013.01); *A61B 2560/0456* (2013.01); *A61B 2562/028* (2013.01)

(58) Field of Classification Search
  CPC ............ A61M 16/0666; A61M 16/085; A61M 16/0858; A61M 16/0866; A61M 16/106; A61M 2202/0208; A61M 2202/0283; A61M 2205/0216; A61M 2205/7536; A61M 2230/432; A61N 2005/0606; A61N 2005/063; A61N 2005/0652; A61N 2005/0659; A61N 5/0603; A61N 5/0613; Y02C 20/10
  See application file for complete search history.

(56) References Cited

U.S. PATENT DOCUMENTS

| | | | | |
|---|---|---|---|---|
| 5,782,234 A * | 7/1998 | Bates | ........ | A62B 23/06 128/204.13 |
| 6,244,865 B1 * | 6/2001 | Nelson | ........ | A61B 5/097 128/205.29 |
| 2006/0137689 A1 * | 6/2006 | Evensson | ........ | A62B 23/06 128/205.27 |
| 2006/0225738 A1 * | 10/2006 | Afentoulopoulos | ........ | A62B 7/10 128/205.27 |
| 2010/0268107 A1 * | 10/2010 | de Heer | ........ | A61B 5/411 600/539 |
| 2011/0218451 A1 * | 9/2011 | Lai | ........ | A61F 5/56 600/533 |
| 2013/0280671 A1 * | 10/2013 | Brawn | ........ | A61N 5/0603 433/24 |
| 2014/0276171 A1 * | 9/2014 | Hestness | ........ | A61B 5/097 600/531 |

* cited by examiner

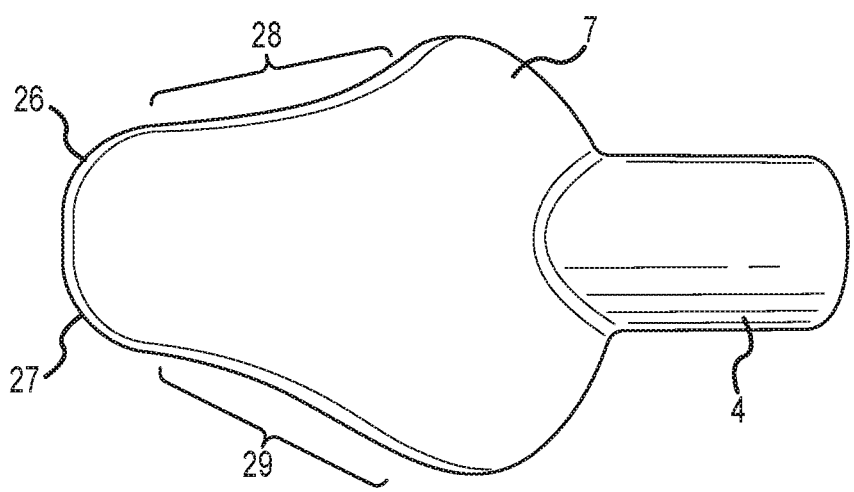
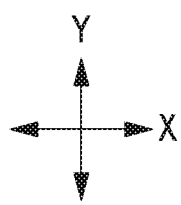
FIG.4

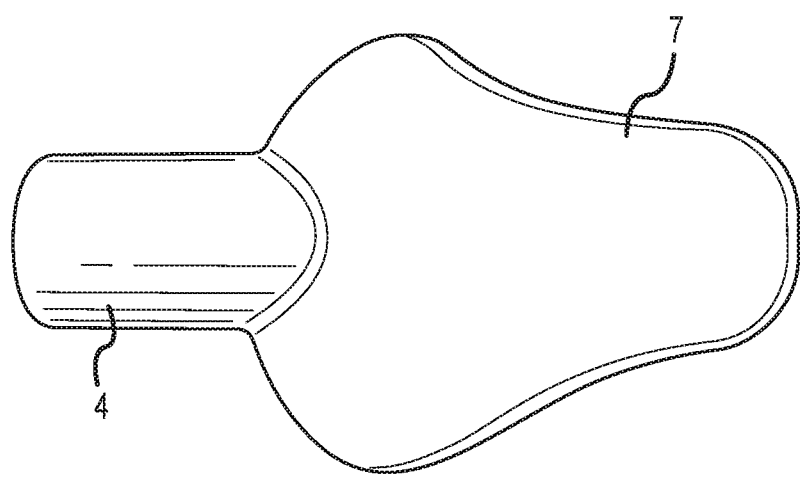
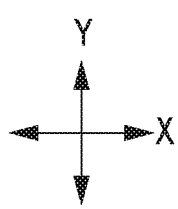
FIG.5

ORAL AND NASAL DEVICES FOR THE TREATMENT OF SLEEP APNEA AND/OR SNORING WITH FILTER AND SENSORS TO PROVIDE REMOTE DIGITAL MONITORING AND REMOTE DATA ANALYSIS

This is a 371 national phase application of PCT/US2015/054559, filed on Oct. 7, 2015 and claims priority to U.S. provisional application 62/060,956 filed on Oct. 7, 2014.

BACKGROUND OF THE INVENTION

There are at least two different types of sleep apnea, including obstructive sleep apnea and central sleep apnea. Obstructive sleep apnea (OSA) is caused by an obstruction of the airway. For example, the soft tissue of the airway may collapse thereby obstructing breathing during sleep. Central sleep apnea syndrome (CSAS) is a sleep-related disorder in which the effort to breathe is diminished or absent, typically for 10 to 30 seconds, either intermittently or in cycles and is usually associated with a reduction in blood oxygen saturation. Central sleep apnea is very rare, and typically resolves when obstructions are treated.

SUMMARY OF THE INVENTION

The present invention includes devices for monitoring, diagnosing or treating sleep apnea in a patient. The device comprises a mouthpiece or a nasal splint; a filter assembly; and a microchip comprising sensors. The filter assembly and the microchip are positioned with the mouthpiece. The filter assembly comprises a filter grid insert and filter flap to create resistance during the patient's inhalation and exhalation. The mouthpiece or the nasal splint may be used together but generally are used individually.

The invention may also provide a system comprising the device and a charging cradle, and a receiving unit such as a computer or smartphone to receive data obtained by the sensors in the mouthpiece or nasal splint. The system also may comprise software or an "app" to analyze the data and prepare a report.

Kits are provided by the invention. A kit may comprise a mouthpiece and/or a nasal splint, a filter assembly, a microchip, at least one filter grid insert and at least one filter flap. The kit may further comprise a recharging cradle to recharge a battery on the microchip.

Embodiments of the invention provide a filter assembly for use in the mouthpiece or nasal splint of the device of the invention. The filter comprises a filter grid, a filter grid insert, and a filter flap to create resistant when the wearer of the mouthpiece inhales or exhales.

Another embodiment of the invention provides a set of nasal splints to be inserted into the nostrils. The splint comprises a structure for dilating the nostrils and a filter assembly. The filter assembly comprises a filter grid insert and filter flap to create resistance during the patient's inhalation and exhalation.

One embodiment provides a system comprising the nasal device and a charging cradle, a receiving unit such as a computer or smartphone to receive data obtained by the sensors in the mouthpiece. The system also may comprise software or an "app" to analyze the data and prepare a report.

Kits are provided by the invention. A kit may comprise a nosepiece, a filter assembly, a microchip, at least one filter grid insert and at least one filter flap. The kit may further comprise a recharging cradle to recharge a battery on the microchip.

Embodiments of the invention provide a filter assembly for use in the nosepiece of the device of the invention. The filter comprises a filter grid, a filter grid insert, and a filter flap to create resistant when the wearer of the mouthpiece inhales or exhales.

Also provided is a method of a method of treating sleep apnea caused by in appropriate over-breathing and improper oxygenation. A patient wears the mouthpiece or nosepiece while sleeping. The filter assembly comprising the filter grid insert and filter flap creates resistance during the patient's inhalation and exhalation which forces the patient to stop over-breathing and achieve proper oxygenation to the body. This in turn allows for proper oxygenation, which precludes the patient's necessity to wake up gasping for air.

BRIEF DESCRIPTION OF THE DRAWINGS

FIG. 4 is a right side view of a mouthpiece of a device of the invention.

FIG. 5 shows a left side view of a mouthpiece of a device of the invention.

FIG. 9B is a left side cross-section view of a mouthpiece of a device of the invention showing a hydration mesh encasing the filter assembly FIG. 10A provides a top cut away view of a filter assembly 31 of the device of the present invention. The outline of the filter grid 41 is provided as a cross sectional view to show the inside of the filter assembly and to show in one embodiment how the wedges 39 fit under the filter grid.

FIG. 10B shows a top sectional view, 10C shows a side sectional view and 10 shows an end view of a laminar flow tube.

FIG. 18 provides figures of an exemplary nasal splint.

DETAILED DESCRIPTION OF THE INVENTION

The present invention provides an anti-snoring and sleep apnea device that comprises in some embodiments a flexible mouthpiece shaped to fit about the teeth of the upper and lower jaw, and also U-shaped in cross section so as to fit between the teeth and lips, with a centered tubular, oval shaped extension for breathing, a disposable bi-directional filter comprising a filter grid insert and a filter flap, a plurality of micro sensors on an electronic circuit board and a rechargeable battery all located within the mouthpiece of the invention.

The present invention also provides an anti-snoring and sleep apnea device that comprises a semi-rigid nasal splint shaped to fit in the nasal airways in a diagonal, cone shaped, or arced spring form.

Mouthpiece

Figure 1:
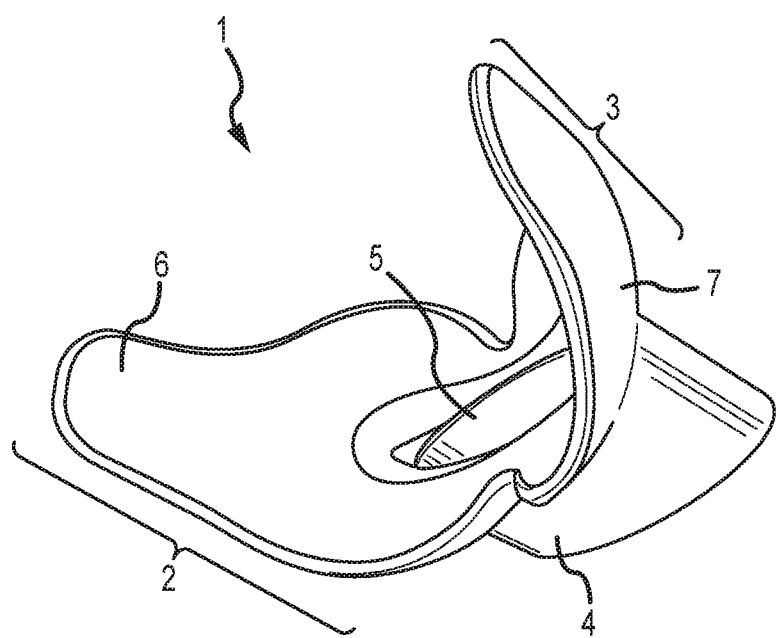
FIG. 1 provides a perspective view of a mouthpiece of a device of the invention.

FIG. 1 shows a depiction of a mouthpiece 1 of a device 100 of the present invention having a left flange 2, a right flange 3, and a centered tubular, oval shaped extension for breathing 4 (referred to herein as a "protuberance") that when worn by a user extends from the mouth though the lips. The protuberance 4 is hollow and defines an air passage 5 that allows air flow through the mouthpiece 1. The mouthpiece 1 has an inner surface 6 and an outer surface 7.

The flanges 2 and 3 may extend along the inside of the user's cheeks and may be at least partially in front of the user's teeth. The inner surface 6 may be facing the user's mouth and the outer surface 7 may be touching or at least partially touching the cheeks and/or lips of the user. In some embodiments, the mouthpiece 1 holds the user's jaw forward to increase airflow.

The user can orient the mouthpiece 1 so that saliva is less likely to flow through the air passage 5, while the user is sleeping on their side. For example, the user may slide the mouthpiece 1 to the upper portion of the mouth.

The flanges 2 and 3 prevent the mouthpiece 1 from being too loose or accidentally falling out of place. The inside surface 6 of the flanges 2 and 3 may be curved. The curved surface of the flange may be configured to hold the air passage 5 in or around the correct location to assist the user in breathing air through the air passage 5. In one example, the inside surface 6 is concave so that the flanges 2 and 3 do not press on the teeth of the user. In some embodiments, the inside surface 6 of the flanges 2 and 3 is flat. The length, height, and thickness of the flanges 2 and 3 may be configured to keep the mouthpiece 1 comfortably in place.

The flanges 2 and 3 may be any length and height. In one example, the flanges 2 and 3 are similar to flanges found on mouth pieces in a snorkel. The flanges 2 and 3 may range, for example, from ¼ inch to ½ inch and the height of the flanges 2 may range from ¼ inch to 1¾ of an inch. In some embodiments, the flanges 2 and 3 may be thick enough to lightly push against the lips of the user to encourage the user's mouth naturally open and reduce bruxism.

In various embodiments, the protuberance 4 and the air passage 5 are located in the center of the mouthpiece 1. Those skilled in the art will appreciate that the protuberance 4 may be located at any place of the mouthpiece 1. In some embodiments, the protuberance 4 is flexibly coupled to the mouthpiece 1 allowing the protuberance 4 to bend in different directions.

The protuberance 4 extends from the flanges 2 and 3. In various embodiments, the protuberance 4 holds the lips of the user open. In one example, the protuberance 4 extends through the lips allowing the user's lips to rest along a portion of the protuberance 4. See FIG. 9. In another example, the protuberance 4 does not extend through the user's lips, but rather extends from the flanges 2 and 3 sufficiently so that the user's lips are held open to allow air to pass through the air passage 5. The protuberance 4 may preferably be oval, but can be in any hollow shape.

Although the protuberance 4 and air passage 5 are depicted as extending directly away from the flanges 2 and 3, those skilled in the art will appreciate that the protuberance 4 and air passage 5 may be constructed at an angle. For example, the protuberance 4 and air passage 5 may be tilted. In one example, the protuberance 4 and air passage 5 may be tilted away from the flanges 2 and 3 and upwards towards the user's nose. The protuberance 4 and air passage 5 may be tilted in any direction. In some embodiments, the mouthpiece 1 is constructed from a material that allows the user to direct the angle of the protuberance 4 and air passage 5.

The protuberance 4 may be at any length extending from the flanges 2 and 3. In one example, the protuberance 4 extends ½ inch from the flanges 2 and 3. In another example, the protuberance 4 extends 1½ inches from the flanges 2 and 3. The protuberance 4 may extend anywhere from ½ inch to 1½ inches from the flanges 2 and 3. Those skilled in the art will appreciate that the protuberance 4 may be any length.

The air passage 5 in the protuberance 4. The air passage 5 allows for the passage of air into and out of the mouth of the user. It will be appreciated by those skilled in the art that the air passage 5 may be any shape, to accommodate the other parts of the device, including the filters and sensors.

In some embodiments, the protuberance 4 may be coupled to a retainer device that is formed to the shape of the user's upper or lower teeth. Alternatively, the protuberance 4 may be coupled to anchors that are cemented to the teeth.

The mouthpiece 1 may comprise any kind of material and may be of any hardness. In some embodiments, the mouthpiece 1 comprises a Shore A hardness with a durometer value between 30 OO and 75 D. It is preferred that the mouthpiece is made of a material that is somewhat flexible that allows the device to flex as the user's mouth moves. The protuberance needs to be formed of a material that is rigid enough so not as to collapse upon pressure of the user's lips and needs to be rigid enough to hold the filter and the sensors.

In non-limiting examples, the mouthpiece 1 may be a thermo-plastic elastomer, silicon material, foam material or any combination. Examples of elastomers include, but are not limited to, rubber, synthetic polyisoprene, butyl rubber, polybutadiene, styrene-butadiene rubber, nitrile rubber, cloroprene rubber, ethylene propylene rubber, ethylene propylene diene rubber, epichlorohydrin rubber, polyacrylic rubber, silicone rubber, fluorosilicone rubber, fluoroelastomers viton, tecnoflon, fluorel, alias and Dai-El, perfluoroelastomers tecnoflon PIR, kalrez, chemraz, and perlast, polyether block amides, chlorosulfonated polyethylene, ethylene-vinyl acetate, thermoplastic elastomers (e.g., elastron), thermoplastic vulcanizates (e.g., santoprene TPV), thermoplastic polyurethane, thermoplastic olefins, proteins resilin and elastin, and polysulfide rubber.

The mouthpiece 1 may be shaped differently than that depicted in the figures. For example, the mouthpiece 1 may comprise a teeth separator (e.g., bite guard) extending from the flange 2 and 3 in a direction away from the protuberance 4. The teeth separator may be a ridge of material that fits between the teeth to keep the teeth apart (e.g., the teeth may rest on the teeth separator) thereby improving air flow and/or reducing bruxism (i.e., teeth grinding). The teeth separator may comprise a single piece of material that extends from the left flange 2, across the air passage 5, to the right flange 3. Alternatively, the teeth separator may comprise two pieces or more of material, each piece extending along at least a portion of a flange 2 or 3 without being over the air passage 5. The teeth separator may be of any shape and may be parallel with the users teeth/jaw line or may be angled (e.g., angled upwards towards the user's upper jaw, or angled downwards). The teeth separator may have any thickness. For example, the teeth separator may be from ¼ inch thick to ⅝ inch thick.

In some embodiments, the mouthpiece 1 is specifically created by a specialist to fit a specific user. In other embodiments, the mouthpiece 1 may be available over the counter. In one example, there may be different sizes to fit different people with different needs (e.g., one model for children, one model for men, and another model for women).

Figure 2:
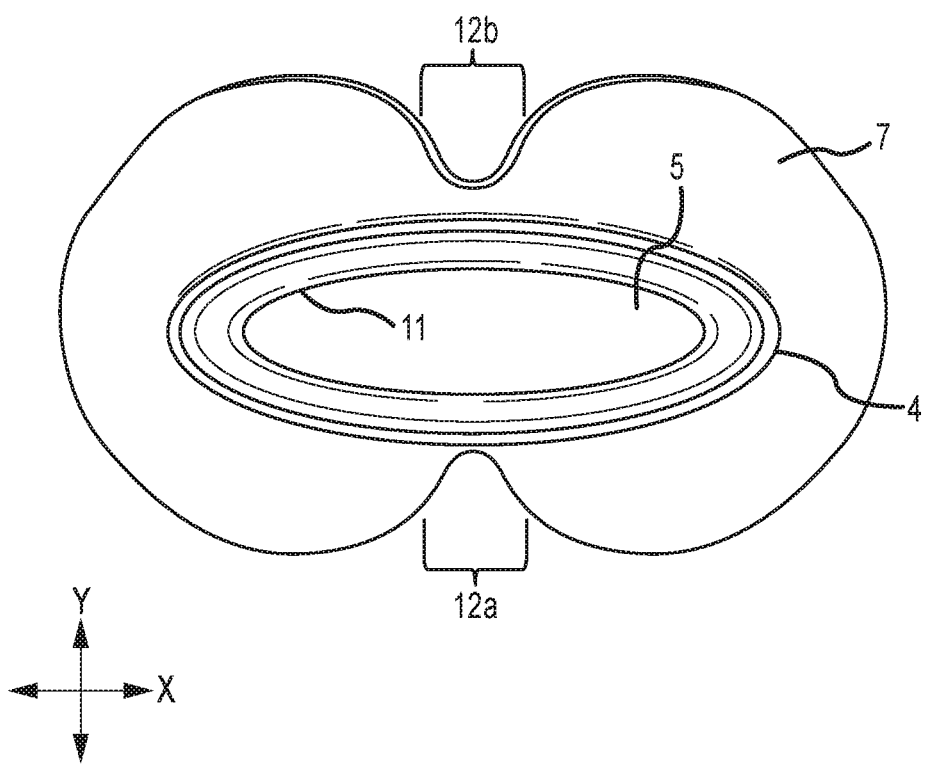
FIG. 2 is a front view of a mouthpiece of a device of the invention.

FIG. 2 is a front view a mouthpiece of a device of the invention. An x axis and a y axis have been depicted for convenience of orientation. The front view of the mouthpiece 1 depicts the air passage 5 through the protuberance 4. A filter ridge 11 and frenulum gaps 12a and 12b are also depicted.

The filter ridge 11 is a ridge in the protuberance 4. The ridge provides a "stop" for the filter when it is placed into the protuberance. The filter ridge 11 may keep the filter in place and prevents the filter from slipping through the back of the protuberance 4. The filter ridge 11 may keep a gap between the filter and the user's teeth. In some embodiments, the gap between the filter and the user's teeth is 1 mm. In various embodiments, the gap may be 1 mm to 1 cm. Those skilled in the art will appreciate that the gap may be any size.

The frenulum gaps 12a and 12b are gaps at the top and bottom of the mouthpiece 1 between the left flange 2 and the right flange 3. A user's frenulum (i.e., the frenulum labii superioris inside the upper lip and the frenulum labii inferioris inside the lower lip) may fit between the frenulum gaps 12a and 12b, respectively. In some embodiments, the frenulum gaps 12a and 12b allow for a comfortable fit within a user's mouth. In one example, the user's frenulum is able to move between the frenulum gaps 12a and 12b. The frenulum gaps 12a and 12b may be of any shape.

The upper frenulum gap 12b is along y axis above x axis. The lower frenulum gap 12a is along the y axis below x axis. In various embodiments, there may be no upper frenulum gap 12b and/or no lower frenulum gap 12a.

Figure 3:
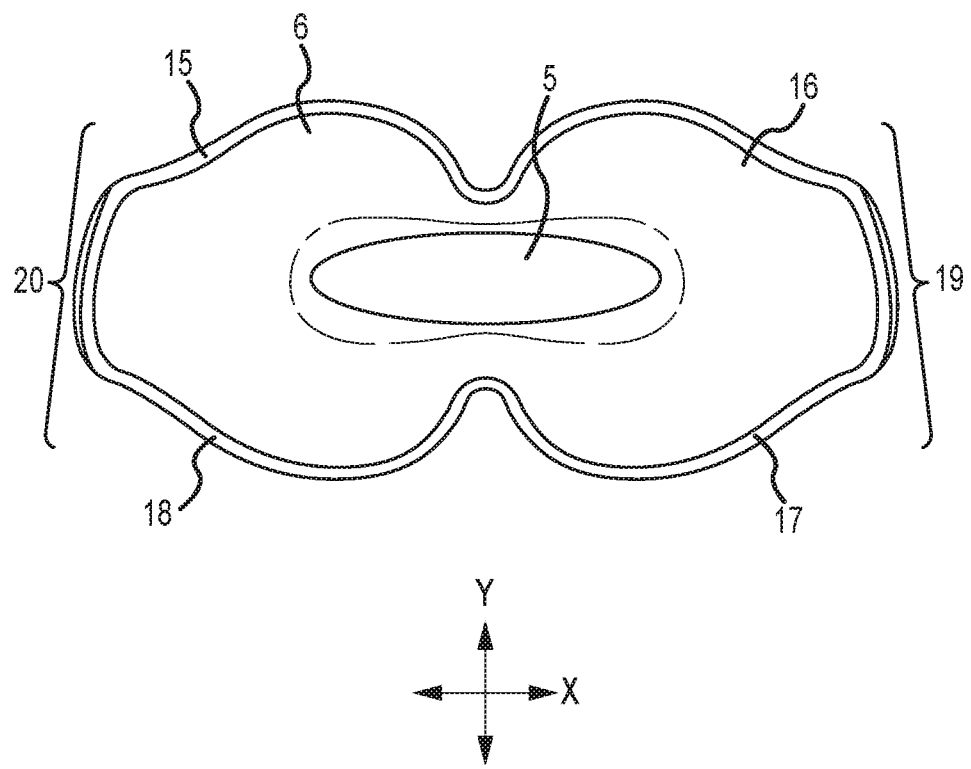
FIG. 3 is a back view of a mouthpiece of a device of the invention.

FIG. 3 is a back view of a mouthpiece of a device of the invention. An x axis and a y axis have been depicted for convenience of orientation. The back view of the mouthpiece 1 depicts the air passage 5 through the protuberance 4.

In some embodiments, the curvature of the upper right flange 16 and/or the curvature of the upper left flange 15 may be curved more or less than the curvature of the lower right flange 17 and/or the curvature of the lower left flange 18. In still other embodiments, the curvature of the upper right flange 16 and/or the upper left flange 15 may be substantially similar to the curvature of the lower right flange 17 and/or the lower left flange 18.

In various embodiments, the left flange and the right flange may have be canted (e.g., the left flange and the right flange may be angled or flared) such that the mouthpiece 1 fits more comfortably in a user's mouth. In one example, the end of the left flange that is opposite the protuberance 4 may be angled to create the cant (i.e., the left flange cant 20). Similarly, the end of the right flange that is opposite the protuberance 4 may be angled to create a cant (i.e., the right flange cant 19). In some embodiments, the flanges of the mouthpiece 1 may be independently adaptable by the user so that the user can create the desired cants. The cants 19 and 20 may allow for the lower jaw to have more latitude to move. The cant may be of any angle. In some embodiments, the cants 19 and 20 are greater than 3 degrees. In various embodiments, the cants 19 and 20 have an angel from 1 to 10 degrees. Those skilled in the art will appreciate that the degree of angle of cant 19 may not be equal to the angle of cant 20. In some embodiments, one or both of the flanges do not have a cant.

In some embodiments, the upper and lower edges of the mouthpiece 1 help to keep the user's teeth along the upper and lower jaw open. By keeping the teeth from clenching, the mouthpiece 1 may reduce grinding. In one example, the upper left flange 15, the upper right flange 16, lower left flange 18, lower right flange 17 may gently press against the user's upper and lower gums; the pressure may increase if the user attempts to close their mouth. As a result, the mouth and/or space between the teeth may be naturally kept slightly open during sleep thereby allowing greater airflow and reduction of negative pressure in the mouth. Further, the open airway may keep the uvula of the user from vibrating.

FIG. 4 is a right side view of an exemplary mouthpiece of a device of the invention. The right side view displays the right flange as well as the protuberance 4. The curvature of the outer surface 7 of the flange may be of any degree. In some embodiments, the outer surface 7 of the right flange is curved such that the top and bottom edge of the right flange may come in contact with the gums or teeth of the user while the rest of the right flange does not contact the user's teeth. Further, the curvature may be such that the lips of the user rest easily against at least a portion of the outer surface. FIG. 4 also depicts the upper curvature of the right flange 28 as well as the lower curvature right flange 29. The upper edge of the right flange 26 and the lower edge of the right flange 27 is also depicted.

In some embodiments, the mouthpiece 1 is symmetrical about the x axis. In one example, the top portion of the right flange above the x axis is similar to the bottom portion of the right flange below the x axis. In other embodiments, the top portion of the right flange above the x axis is not similar to the bottom portion of the right flange below the x axis.

Similarly, the top portion of the left flange above the x axis may be similar to the bottom portion of the left flange below the x axis. In other embodiments, the top portion of the left flange above the x axis is not similar to the bottom portion of the left flange below the x axis. Further, the mouthpiece 1 may be symmetrical across the y axis. For example, the left flange may be similar to the right flange. In other embodiments, the left flange may be dissimilar to the right flange.

Figure 6:
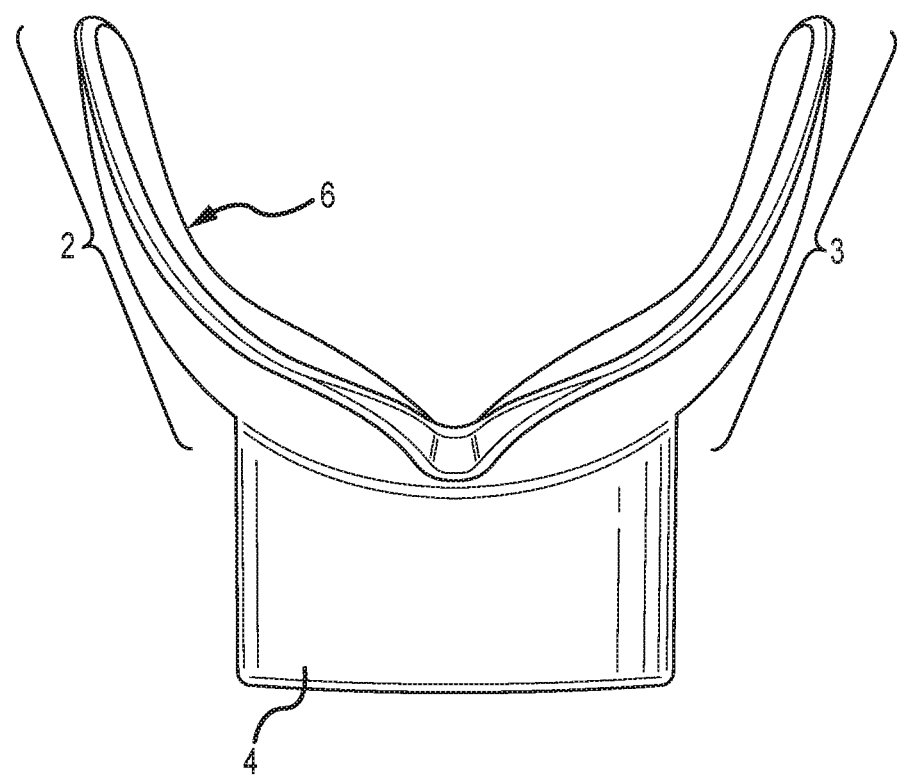
FIG. 6 shows a top view of a mouthpiece of a device of the invention.

FIG. 6 is a top view of a mouthpiece of the present invention. From the top view, the lower portion of the inside surface 6 of the mouthpiece 1 is viewable because of the cant of the left flange 2 and the cant of the right flange 3.

Figure 7:
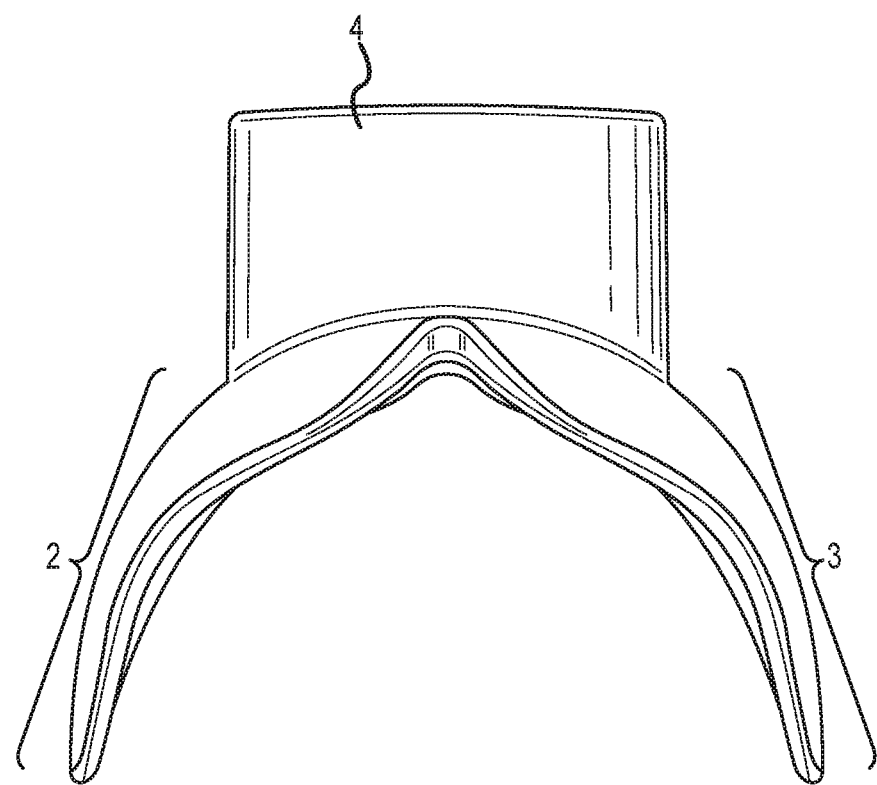
FIG. 7 is a bottom view of a mouthpiece of a device of the invention

FIG. 7 is a bottom view of a mouthpiece of a device of the invention.

In some embodiments, the mouthpiece 1 may be held on the user's head with a head strap to limit or eliminate shifting during sleep. The strap may also improve the seal between the user's mouth and the device. In another example, the head strap is configured to hold all or a portion of the mouthpiece 1 in place outside of the user's mouth.

In various embodiments, the mouthpiece 1 is configured to hold the user's jaw in a forward position. In one example, a teeth separator is configured to push out the user's jaw and additional airflow is allowed to pass (e.g., through air holes). In another example, the teeth separator is configured to push out the user's jaw and the flange is reduced or eliminated to allow additional air flow into the mouth.

The mouthpiece 1 may also be modified to hold the user's tongue during epileptic seizures so the tongue does not get bitten nor is allowed to slide to the back of the throat and block the airway.

In various embodiments, the mouthpiece 1 of the device may be coupled to one or more other devices. In one example, the protuberance 4 may be coupled with a humidifier that moistens air flowing through the air passage 5. In another example, the protuberance 4 may be coupled with a dehumidifier, nebulizer, and/or other devices. The mouthpiece 1 may be coupled to a suction device. In some embodiments, the protuberance 4 is coupled to a suction device that applies negative pressure to the airway. In one example, the nasal passages may be plugged to create suction in the mouth. The negative pressure may increase the amount of air that the user exhales. Improved exhalation improves the extraction of $CO_2$ from the lungs and increases oxygen flow into the lungs to reduce poor breathing, which can lead to conditions such as metabolic acidosis which can lead to coma or death.

The mouthpiece may have a nasal cannula attached thereto.

The mouth piece may have a notch or a bump or some other marking to allow the user to feel and identify the top of the mouthpiece in the dark.

The mouthpiece may be coated with a material comprising carbon or silicone nanotubes, which can be used, for example, to detect electrical signals from the mouth.

In certain embodiments, the mouthpiece may be encompassed by a mesh material (e.g. Polylactide Acid (PLA) that can be moistened to provide a humid environment in the mouth of the user so the user does not develop an uncomfortable mouth dryness while wearing the device.

Filters

Figure 8:
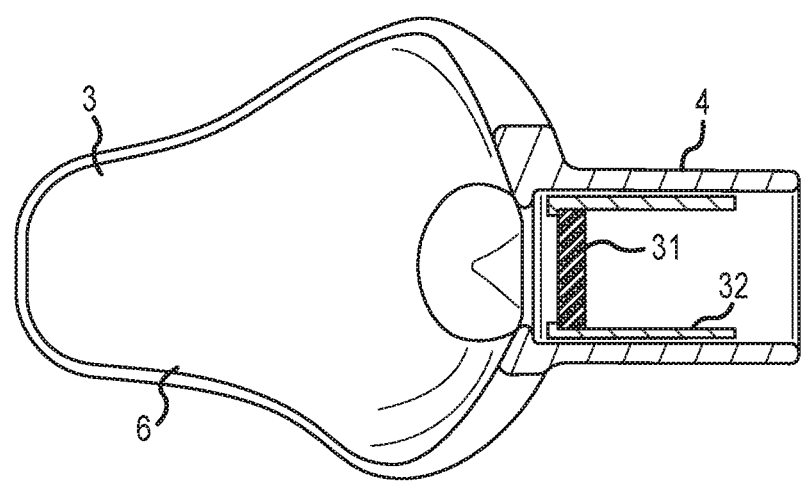
FIG. 8 is a right cross-section view of a mouthpiece of a device of the invention.

Devices of the invention further comprise a bi-directional filter assembly that fits inside the protuberance 4 of the mouthpiece. The filter assembly may be disposable or may be sterilized or sanitized. FIG. 8 is a right cross-section view of a mouthpiece of a device of the invention showing a filter assembly 31. The cross-section view depicts the right flange 3, the inner surface 6, and the protuberance 4. Inside the protuberance 4, a filter assembly 31 and ring 32 is depicted. The ring 32 fits within the protuberance 4 and holds the filter assembly 31.

Depictions of the exemplary filters assembly design are provided in FIGS. 10-15. The filter assembly has a bi-directional valve system built into it. The purpose of the filter assembly is to create a point of resistance in the airway that artificially limits the amount of air that can flow in either direction. This reduces the amount of carbon dioxide that can be exhaled, causes the user to retain more $CO_2$, thus helping the body maintain optimal levels of $CO_2$, which helps oxygenate the organs via the Bohr Effect. Further, optimal $CO_2$ levels also help the body regulate the impulse to breathe.

The filter assembly is made of Polyethylene, and Polylactide Acid (PLA). They can also be made of other materials such as Polyethylene, Somos, or other materials that are mostly rigid with some elasticity.

The filter assembly is preferably made of a material that can be sanitized and/or sterilized. In certain embodiments the filter assembly is disposable. They would be replaced or cleansed as needed. The filter assembly is bi-directional in that air can flow in an out of them. Preferably the filter assembly is designed so that exhalation through the filter requires more effort than inhalation through the filter.

Figure 10A:
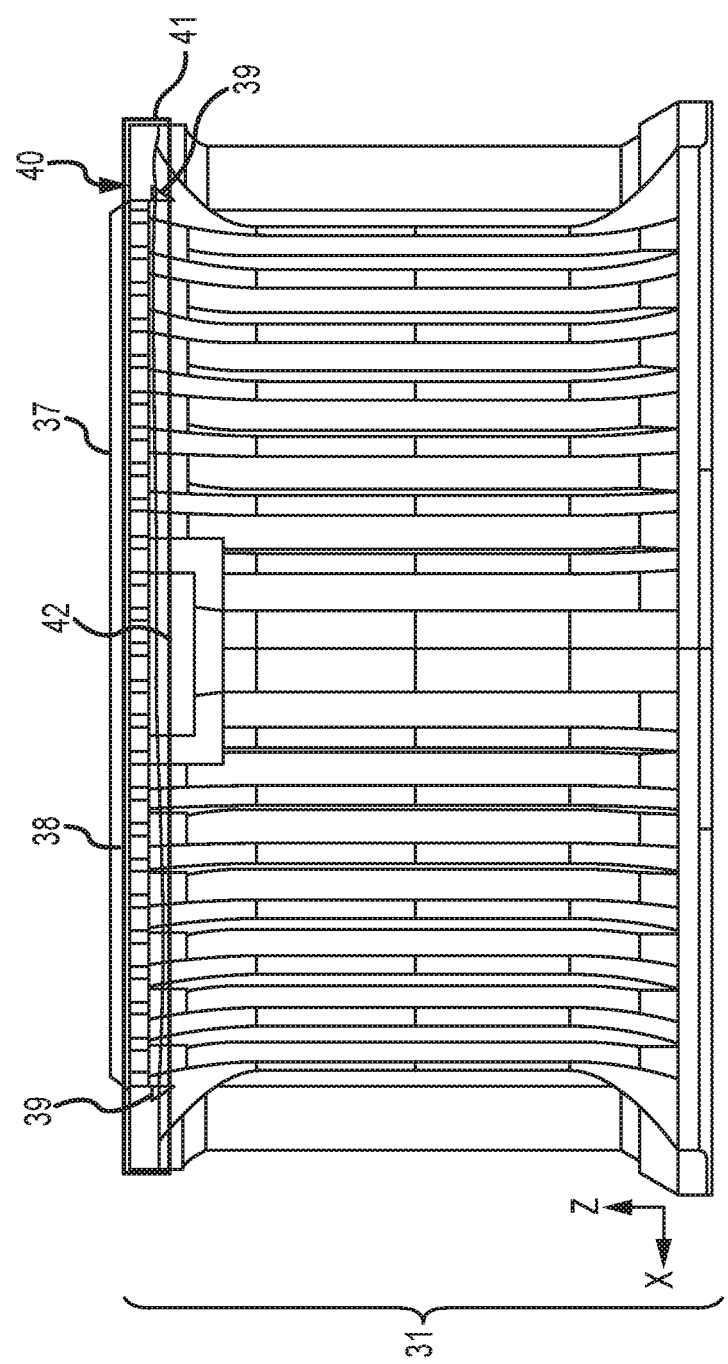
FIGS. 10B, 10C and 10D provide another embodiment of a filter assembly which comprises laminar flow tubes.

The filter assembly has two adjustable/interchangeable parts, the filter grid insert and filter flap. FIG. 10A provides a top cut away view of a filter assembly 31 of the device of the present invention. FIG. 10A provides a top cut away view of a filter assembly 31 of the device of the present invention. The outline of the filter grid 41 is provided as a cross sectional view to show the inside of the filter assembly and to show in one embodiment how the wedges 39 fit under the filter grid.

There is a bit of "play" 38 under the filter flap so that when the user inhales, the flap is pulled away from the filter grid insert and when the user exhales, the flap is pressed against the filter grid insert to increase air resistance. The filter flap is attached to the filter face plate 40 of the filter grid. FIG. 10 shows one embodiment where small wedges (39) attached to ends of the filter flap 37 anchors the filter flap to the filter face plate of the filter grid. The filter flap can be any size that can fit within the confines of the face plate of the filter assembly. In certain embodiments, the filter flap is typically ³⁄₃₂" wide, and nearly as long as the filter insert. The filter flap is nearly as long as the longest dimension of the filter insert. FIG. 10 is a sectional view of the filter insert part that fits into the tube (protuberance) in the mouthpiece.

FIG. 10A also shows slot 42 where in certain embodiments, the filter grid insert is slid in behind the filter grid. The filter grid insert is, in certain embodiments, a solid plastic material that purposefully obstructs incoming and outgoing air flow (i.e. inhalation and exhalation). The size of the filter grid dictates the amount of resistance to the air flow. The larger the filter grid insert, the more resistance is created. In another embodiment, the slot is larger and can accommodate a larger filter that can be sized to "cover" the entire filter grid. In this instance, the resistance can be varied by the number and/or size of holes within the filter grid insert. The more dense (less holes) or smaller holes in the filter grid insert would have a greater resistance than a less dense or (more holes) or larger holes in the filter grid insert would have an easier resistance to the airflow.

In some embodiments, instead of using a filter grid insert, holes in the filter grid assembly are plugged to reduce air flow. In some embodiments, air flow can be manipulated by removing orthogonal grid members from the grid insert track and/or from under the filter flap.

Figure 11:
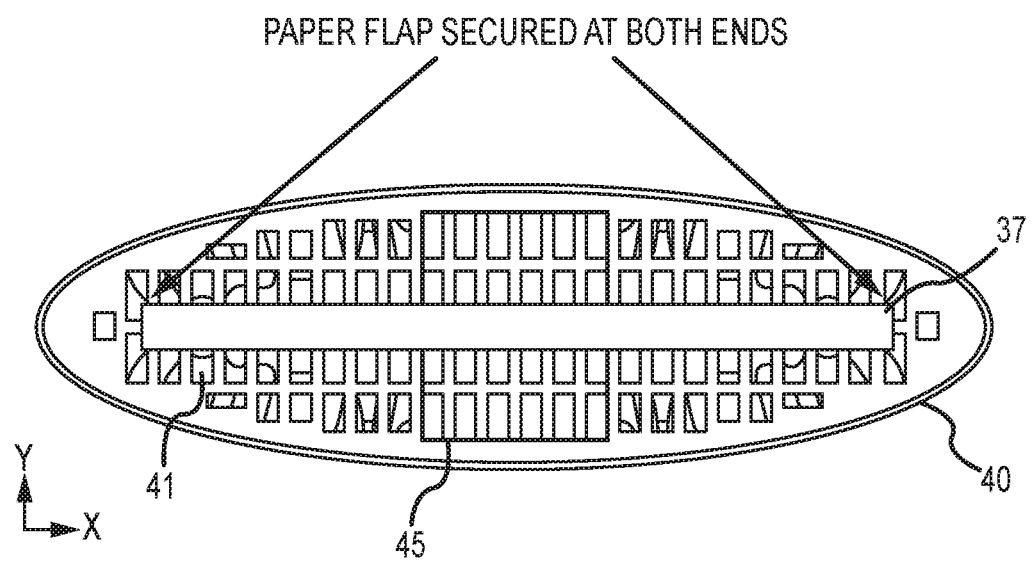
FIG. 11 is a rear view of a filter assembly, which is the end nearest the mouthpiece wearer's mouth. The figure shows a filter flap 37 secured at both ends on top of the filter face plate 40. The filter grid 41 is the surface with the rectangular holes in it. The outline of the filter grid insert is shown. An outline 45 of where the filter grid insert would be positioned behind the filter flap and filter grid is shown.

FIG. 11 is a rear view of a filter assembly, which is the end nearest the mouthpiece wearer's mouth. The figure shows a filter flap 37 secured at both ends on top of the filter face plate 40. The outline 45 of where the filter grid insert would be inserted behind the filter grid can be seen.

Figure 12:
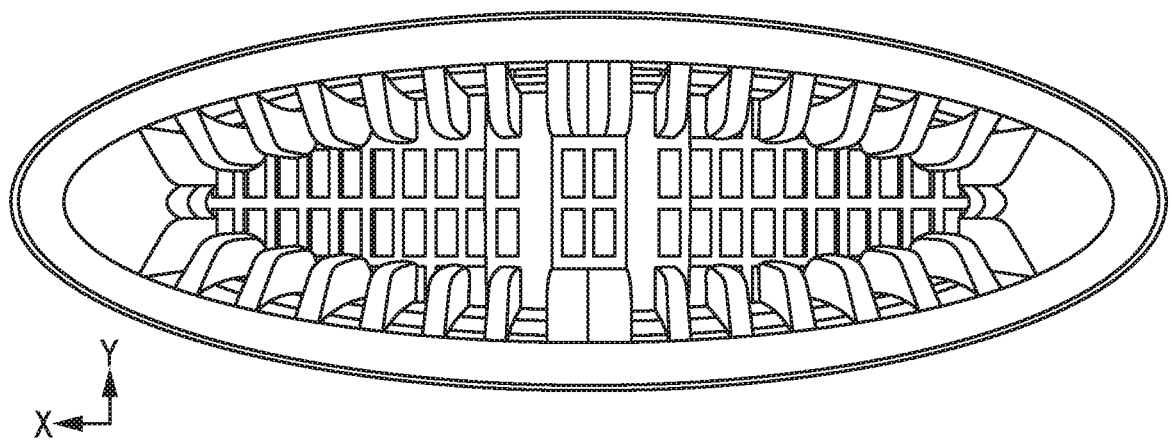
FIG. 12 is a front view of a filter assembly, which is the end farthest away from mouthpiece wearer's mouth.

FIG. 12 is a front view of a filter assembly, which is the end farthest away from mouthpiece wearer's mouth.

Figure 13:
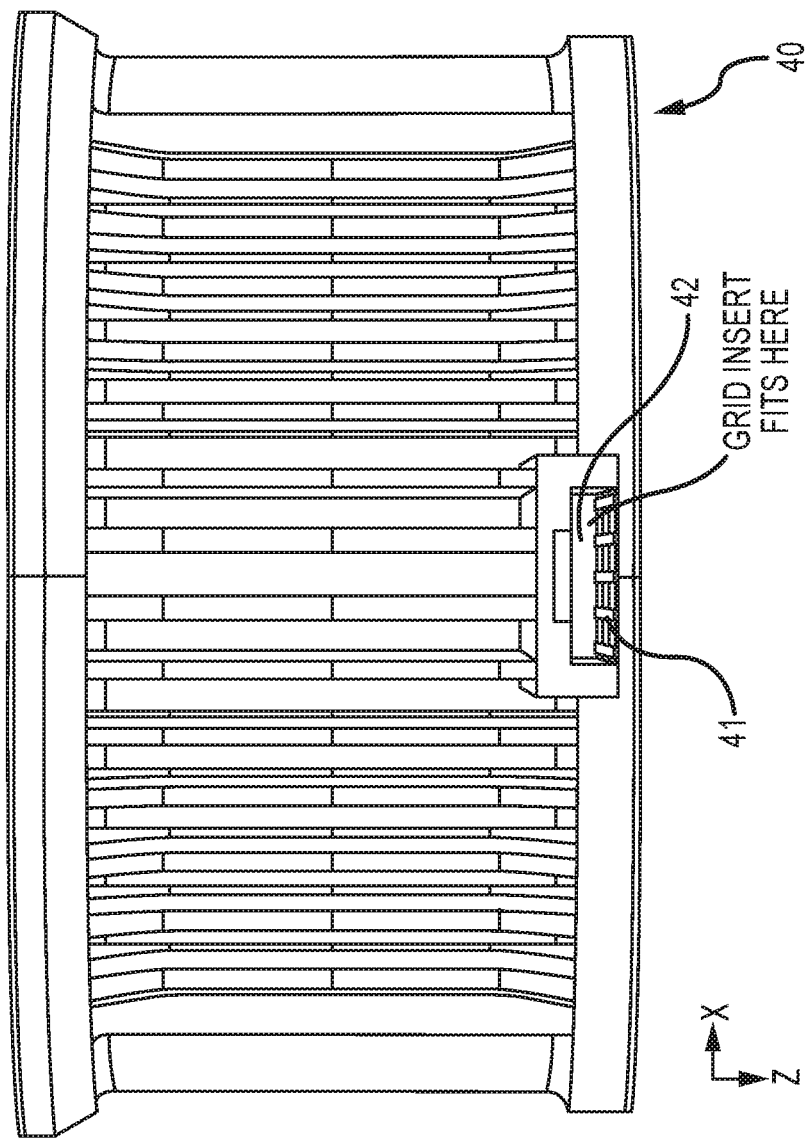
FIG. 13 is a top view of a filter assembly showing the filter grid insert slot 42. The filter grid insert is inserted just behind the filter face plate 40. A portion of the filter grid 41 can be seen through the slot.

FIG. 13 is a top view of a filter assembly showing a cut away of a slot 42 where the filter grid insert can be inserted just behind the filter face plate 40. In the cut away view, the filter grid 41 can be seen.

Figure 14:
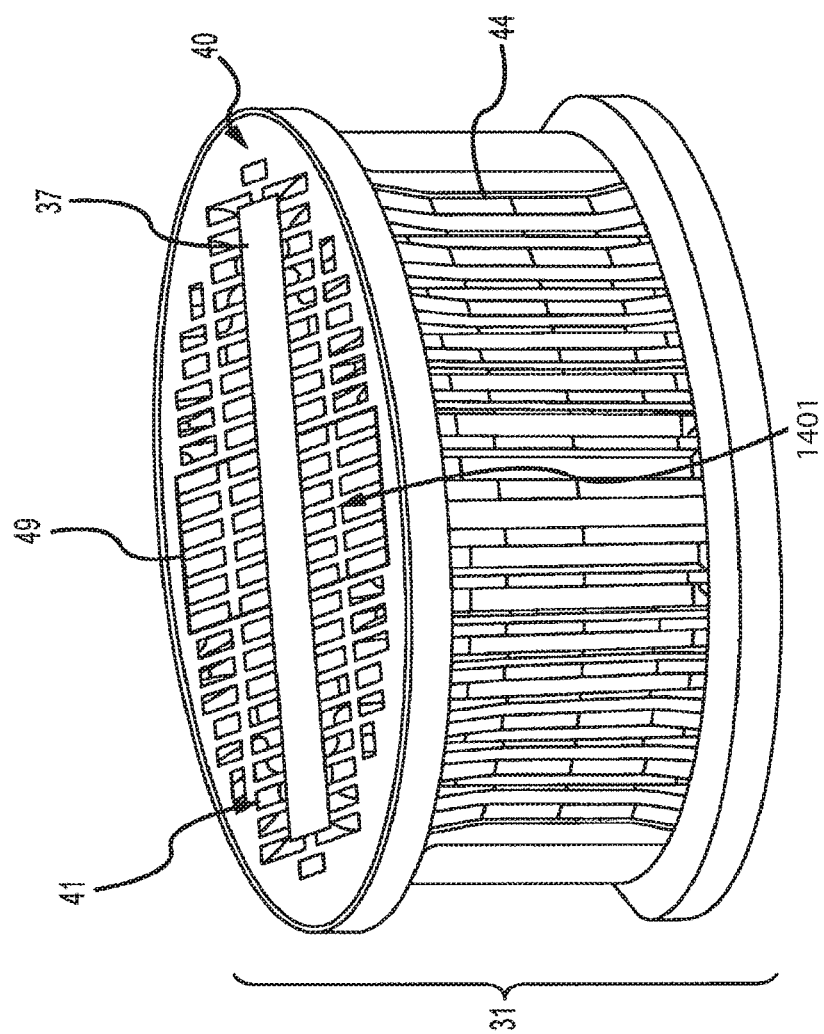
FIG. 14 is a photograph of a filter assembly, showing the filter face plate 40 of the filter grid 41, the outline 49 of the filter grid insert and a filter flap 37. The assembly would be inserted into the mouthpiece so that the filter face plate of the filter grid and the filter grid insert and filter flap are positioned nearest the user's mouth. A hydrating mesh that encompasses the filter insert is shown 44.

FIG. 14 is a photograph of a filter assembly, showing the filter face plate 40 and the filter flap 37. The assembly would be inserted into the mouthpiece so that the filter grid and filter flap are positioned nearest the user's mouth. The outline 49 of where the filter grid insert would be positioned behind the filter face plate is shown. The hydrating mesh is shown "wrapped around" the filer assembly. The filer grid insert 1401 is shown as well.

Figure 15:
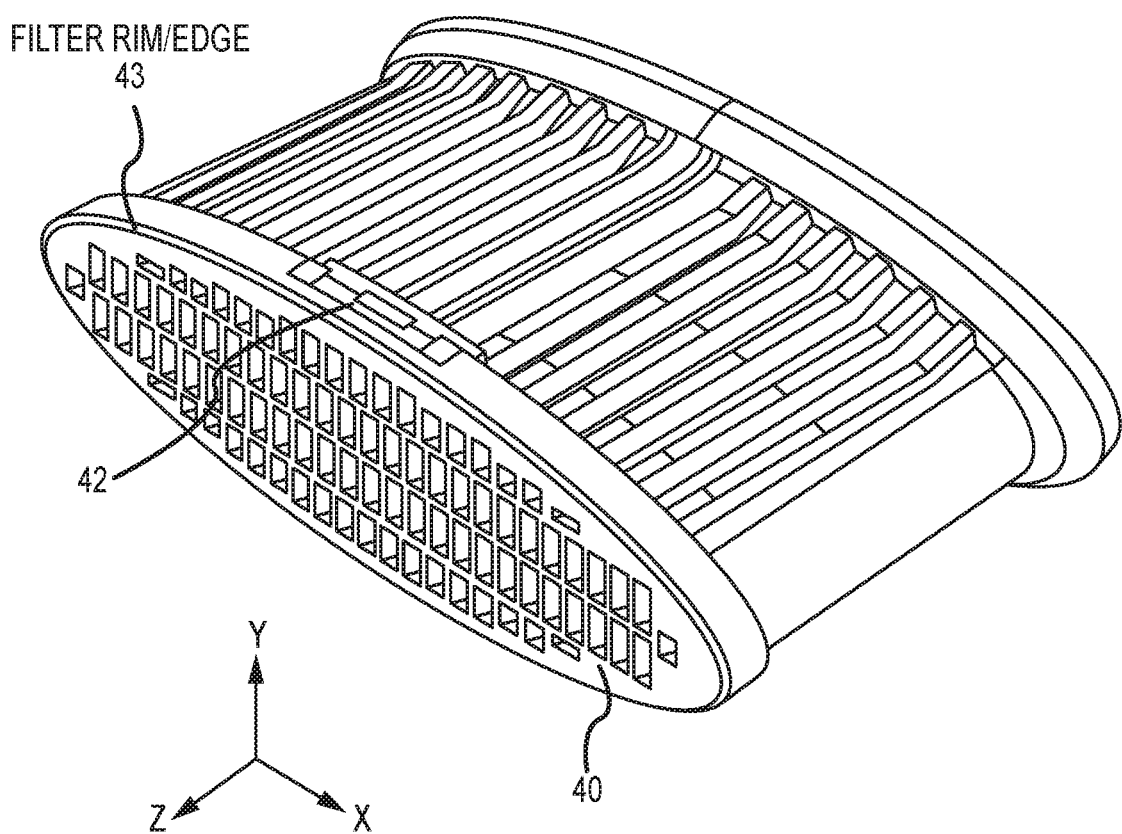
FIG. 15 provides a perspective view of the filter showing the filter face plate 40 and an edge/rim of a filter grid. The slot 42 is also shown.

In some embodiments, the orientation is reversed so the filter grid and filter flap are positioned at the end away from the user's mouth. FIG. 15 provides a perspective view of the filter showing the filter face plate 40 and the edge/rim 43 of the filter grid. The filter grid insert slides into a track through the slot 42. The slot can be placed so the filter grid insert is slid in from the top, bottom or side of the filter faceplate. The filter grid insert can be any size that fits within the confines of the face plate of the filter assembly. In certain embodiments, it is typically about 4/32" long and as wide as the track. In another embodiment, the grid insert is larger and extends to cover the entire area of the filter face plate or is smaller than the entire area of the filter face plate.

The figures show a filter grid insert sliding into the filter assembly behind filter grid but in certain embodiments, the filter grid insert can be positioned in place behind the face plate with other attachment mechanisms. For example, in certain embodiments the filter grid is "snapped" onto the filter assembly, holding the filter grid insert into place between the filter and the rest of the filter assembly. In certain embodiments, the filter grid insert and the filter grid are manufactured as one piece (i.e. the filter grid insert is not independent of the filter grid). In certain embodiments, the filter grid can be manufactured in such a way that sections can be broken off to adjust the air flow. In another embodiment, holes can be drilled in the filter grid to adjust airflow. In still another embodiment, a glue like material, or putty-like material, or solid material can be inserted into the holes in the filter grid to adjust the air flow.

The filter grid insert and filter flap would be adjusted according to the physiological needs of the user, such as physical strength, overall health, known respiratory restriction/obstruction, airway structure, and the like. For example, a person with strong lung strength, and not having much if any respiratory restrictions/obstructions may use a filter grid insert that is larger (extends to cover more area of the filter face plate) and/or is more dense and/or may have a grid flap that is larger and thicker or denser than a person having weak lung strength would use.

In the filter assembly, either the filter grid insert or filter flap or both can be removed and replaced with different filter grid inserts or filter flaps. The filter grid insert and filter flap are designed to optimize the intake of oxygen and expelling of carbon dioxide. For example, either the user obtains a different filter assembly having a different grid insert and filter flap or alternatively simply replaces the current filter grid insert and/or filter flap into the filter assembly. In other words, the entire filter assembly can be replaced or just the filter grid insert and/or filter flap can be replaced. Optimizing carbon dioxide is important because it promotes homeostasis. When carbon dioxide is out of balance, many health conditions can develop.

The filter grids insert can vary on the required effort/resistance to inhale and exhale through them. For example, "easy resistance filter grid inserts" require less effort to inhale and exhale through the filter grid insert, and "difficult resistance filters" require more effort to inhale and exhale through the filter grid insert. The filter flap is not designed to create a significant amount of mechanical resistance. It is designed to reduce hyperventilation. The filter flap creates sufficient air resistance to mitigate hyperventilation. Mitigating hyperventilation reduces the amount of $CO_2$ that is exhaled, thus helping the user maintain optimal levels of $CO_2$ for homeostasis.

The device has to be titrated for each user. Not every user would need the same filter grid insert. Nor would the same filter grid insert work for the same individual at all times. For example, if a patient usually needed a certain resistance filter grid insert but was suffering from a chest or head cold, that user may need to step down to an easier resistance filter grid insert during this time. As another example, a user who has obtained an increased lung fitness over the course of treatment due to increased exercise and weight loss, may need to change to a different resistance filter grid insert. As will be later discussed, the system of the invention that utilizes these devices obtains biofeedback information from sensors within the mouthpiece or nasal splint and provides feedback based on the readings. This feedback is reported to the user and/or the physician to provide guidance as to the appropriate resistance filter grid insert that should be employed.

Accordingly, there is provided a process for calibrating the filter insert. A baseline polysomnogram is performed, either in a sleep lab, or with a home sleep study testing device. Then a second polysonmogram is performed with the breathing device of the invention. The results of the two polysomnograms are compared. If there signs of low carbon dioxide, snoring, or apnea persist, the breathing device is adjusted to increase expiratory resistance. If the results show that the patient is unable to get enough oxygen, then inspiratory resistance is decreased.

As shown in FIG. 8, the filter assembly 31 may fit into a ring 32 that is inserted into the protuberance. In certain embodiments, the user manually inserts the ring and filter assembly within the protuberance 4. In one example, the ring 32 and filter assembly 31 may be removed and another ring 32 and filter assembly 31 may be placed within the protuberance 4. In certain embodiments, the filter assembly is not placed into a ring support structure but is placed directly into the protuberance.

In other embodiments, the ring 32 and filter assembly 31 is designed within the mouthpiece 1 and is not inserted by the user.

Figure 9A:
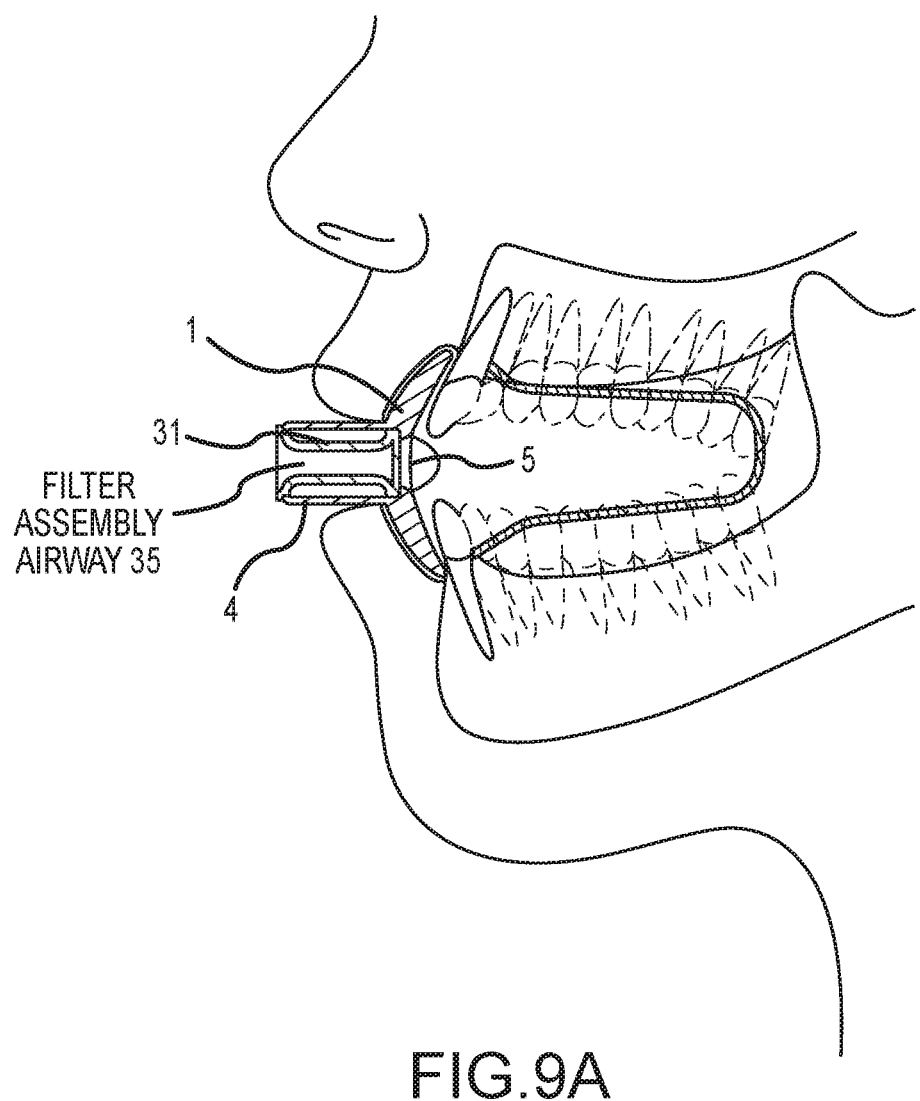
FIG. 9A is a left side cross-section view of a mouthpiece of a device of the invention being worn by a user.

Although FIG. 8 depicts the filter assembly as being at one end of the ring 32, those skilled in the art will appreciate that the filter assembly 31 may be any size and may fill the ring 32 or the entire protuberance. FIG. 9A provides a view of the mouthpiece being worn by a user. In this view the filter assembly is shown as being the entire length of the protuberance 4.

In some embodiments, one can adjust the gap between the filter grid and the teeth to vary the respiratory resistance (in combination or not) with filters described herein.

Figure 9B:
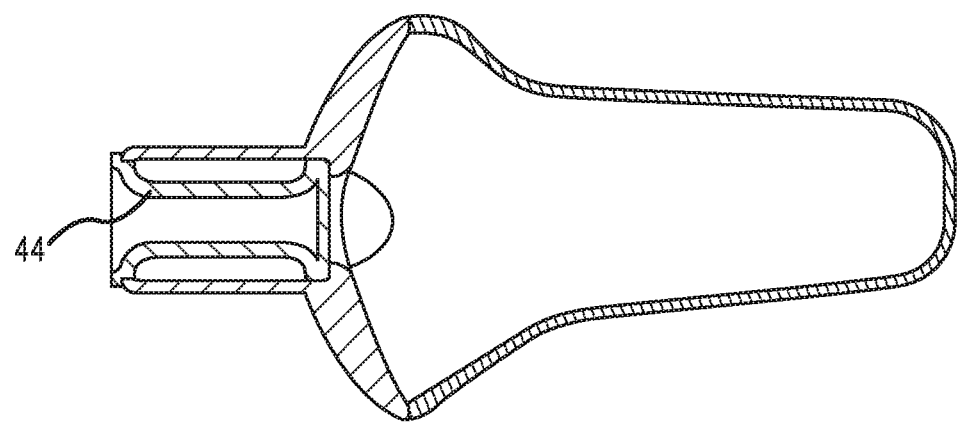
FIG. 9B is 9A is a left side cross-section view of a mouthpiece of a device of the invention.

FIG. 9B shows a hydrating mesh 44 that wraps the outside surface of the filter assembly. The hydrating mesh is made of material that can be wetted so that it moisturizes the air as it is inhaled. In certain embodiments, the entire exterior surface of the mouthpiece can be wrapped with the hydrating mesh.

The filter assembly placed within the protuberance 4 of the mouthpiece of the device optimizes or substantially optimizes esophageal pressure by creating an amount of aerodynamic drag in the protuberance/filter assembly.

Esophageal pressure is created naturally by the sinuses when a user breathes through their nose. The sinuses increase air resistance by roughly 50%. Esophageal air pressure causes the sinuses to release Nitric Oxide (NO). The amount of NO released by the sinuses increases with the amount of esophageal pressure. NO is a bronchodilator, anti-bacterial, and vasodilator. NO and $CO_2$ create complementary health effects. Optimal $CO_2$ causes the muscles around the airway to relax. Optimal $CO_2$ also causes the smooth muscles around blood vessels to relax. Decreased $CO_2$ can also cause the airway to constrict.

The filter assembly may comprise one or more holes that allow saliva to be forced out by air pressure. The holes of the filter may be of any diameter. For example, the holes of the air filter may be as small as 1 mm. If there are multiple holes, the sum of the holes may correlate to the user's lung strength as discussed herein.

The mouthpiece is shown having a filter ridge that acts as a "stop" to prevent the user from forcing the filter assembly too far into the protuberance. See FIG. 2. In certain embodiments, the filter ridge 11 is optional. For example, other design modifications or different filter assembly shapes can be made to constrict the protuberance on the end closest to the mouth of the user so as to prevent the filter assembly from being inserted too far into the mouthpiece.

Figure 10B:
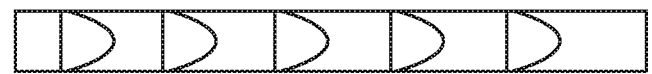
Figure 10C:
Figure 10D:

In another embodiment the filter assembly comprises a filter insert that employs laminar air resistance. The filter insert comprises a plurality of protuberances. The longer the protuberances, the more air resistance is created. FIGS. 10B-10D show views of certain laminar tubes of an exemplary filter assembly. Several of the tubes shown may be assembled into a unified assembly.

In certain embodiments, instead of a filter flap, the filter assembly further may comprise a flap/gate at the end of the filter that would flip up out of the air pathway during exhalation to create more expiratory resistance and would flip or fold down upon inhalation.

In some embodiments, the filter is comprised of an electrically activated material in order to control the level of inspiratory and expiratory resistance, such as carbon nanotubes or dielectric elastomers. For example, carbon nanotubes can be fabricated into multi-walled carbon nanotubes (MWNTs) and bundles of MWNTs that can be mechanically manipulated by electricity. In addition, carbon nanotubes can be grown onto sheets and used as electrical actuators. Carbon nanotubes are very good conductors of electricity and heat and are strong and elastic in certain directions. It has been reported that electrical actuators can be made from films of dielectric elastomers that compressed when voltage was applied. See Pelrine, R. et al., Science Vol. 287, p. 836-838 (2000). So a filter could be constructed of this material and to compress the portions of the filters to allow for more air to flow, an electrical voltage could be applied.

Microchip and Sensors

In devices of the invention, a flexible microchip comprising NEMS/ or MEMS/ASICS is folded and then positioned into an external component of the mouthpiece. NEMS stands for nano electrical mechanical systems. MEMS stands for micro electro mechanical systems (MEMS) that comprises a central unit that processes data (a microprocessor) and a plurality of microsensors. ASIC stands for Application Specific Integrated Circuit device. The microchip can be single or double sided. The microchip is basically a system on a chip (discussed in more detail below). In certain embodiments, the microchip is located between the protuberance of the mouthpiece and the filter insert. Some of the sensors will need direct access to the surface/substance they are monitoring. In this case, there is a hole in the mouthpiece that allows direct access. In certain embodiments the microchip is positioned in the flange of the mouthpiece. In certain embodiments, the microchip is embedded within the protuberance. The microchip may have sensors requiring direct contact with the wearer's lips or inside of mouth so placement within the mouthpiece should be where certain sensors have the necessary contact. With certain sensors, contact between the user's flesh is necessary and in this case, the portion of the mouthpiece housing the microchip would have microholes to allow contact with the inside of the user's lips or mouth, with the sensor. In addition the microchip may be positioned/designed so that certain sensors when inserted into the mouthpiece have access to the airway (flow of air coming in and out of the user's mouth).

The microchip is a system on a chip so it would also house a memory device, such as flash memory, upon which to store data generated by the sensors.

The microchip may also comprise a wireless transmitter upon which the data received from the sensor and stored on the microchip can be wirelessly transmitted to a computer, tablet, smart phone, etc. In certain embodiments the transmission is through Bluetooth RF. The data may be sent to a receiving device (such as but not limited to a computer, tablet, smart phone, etc.) via a wired transmission when the mouthpiece is placed onto a recharging cradle that may be linked to the receiving device through a cable.

The microchip may further comprise a rechargeable battery, such as a lithium rechargeable battery, to supply power to the microchip and the sensors. Preferably a rechargeable lithium battery that has a low current draw that can last up to 7 days is employed. In certain embodiments, the battery can be periodically recharged though magnetic induction. In certain embodiments there is provided a "charging cradle" upon which the user places the device after use to be recharged. The charging cradle can be connected to a power source or a solar device that provides power to recharge the batteries. Further, as mentioned above, the charging cradle may be wired to the receiving device to provide wired transmission of data.

The microchip or the mouthpiece may have an indicator light that changes color or illuminates or emits a tone when it requires charging, or is fully charged.

In certain embodiments and discussed in more detail below, while the device is in the charging cradle, the data obtained during the user's use of the device is transmitted to a receiving device. The mouthpiece may also have an indicator light that changes color or illuminates or emits a tone when the data has been fully transmitted to a receiving device. In certain embodiments, the data is periodically or continuously transmitted to the receiving device.

In certain embodiments, the charging cradle also serves as a UV disinfectant cradle where the device may be sanitized/disinfected. For example, it may be exposed to a certain UV light to disinfect the mouthpiece and the filter assembly, or soaked in a disinfectant solution, such as, but not limited to an antibacterial mouthwash.

In certain embodiments, the microchip further comprises a static IP address so that that the data obtained by the sensors can be "linked" or identified by the IP address when processed later by a processor and further developed into a report that can be sent back to the receiving device for the user's review.

The microchip may also comprise a clock or other time keeping/measuring device.

The plurality of sensors may include sensors that can measure/detect various parameters normally measured when studying a patient for the presence of a sleep disorder such as sleep apnea. As non-limiting examples, respiratory, cardiac, snoring, and body movement components may be measured by the sensors. Signals received from these sensors are then stored and eventually processed into a report (see later discussion). Sensors can include, but are not limited to an oxygen sensor, a carbon dioxide sensor, a pulse sensor, a blood pressure sensor, a core body temperature sensor, an accelerometer/actimetry sensor (for detecting gross motor movements), airflow sensor, sound sensor, end tidal $CO_2$, ECG, EMG, sound, motion via actigraphy, piezoelectric sensors, respiratory inductance plethysomnography, breath speed, saliva pH, etc. Biochemical sensors can be used to detect changes in pH, hormone levels, minerals, electrolytes, amino acids and the like. A vitamin D3 sensor can be used to monitor and in conjunction with UVB LED light used to balance D3 levels. D3 is a hormone that is believed to be important in regulating sleep, weight gain, and paralysis of the throat muscles during sleep.

In addition, sensors that can detect volatile organic compounds (VOCs) could also be included that can be used in detecting or diagnosing the presence of certain biomarkers indicating the presence of a disease. More than 2,000 VOCs have been identified in the human breath that can be considered normal, but even some of these volatiles can indicate a disease condition (somewhere in the body) if elevated or decreased concentrations are found in the breath. Some of the most common (normal) exhaled breath metabolites found in healthy individuals include the major atmospheric unmodified exogenous gases, such as nitrogen (72% by volume), oxygen (reduced from 21% inhaled to about 15% exhaled), carbon dioxide (about 5%), water vapor (about 6% at saturation) and argon (about 1%). In addition to these major normal gases, other common endogenous VOCs include ammonia, acetone, ethanol, methanol, propanol, acetaldehyde and isoprene. Ammonia was found to be a major breath metabolite, measured at a concentration of 833 ppb, followed by acetone (477 ppb), methanol (461 ppb), ethanol (112 ppb), isoprene (106 ppb), acetaldehyde (22 ppb) and propanol (18 ppb).

A wide range of abnormal VOCs, discovered as possible biomarkers of various human diseases, are members of a large diversity of organic chemical classes. Some of the more common chemical classes to which disease biomarker VOCs belong include aliphatic hydrocarbons, aromatic hydrocarbons, alcohols, aldehydes, carboxylic acids (organic acids), esters, ethers, heterocyclic hydrocarbons, ketones, nitriles, sulfides and terpenoids or isoprenoids (terpenes and derivatives). Different classes of VOCs have many different physicochemical properties that largely determine their distribution, adverse effects and retention in the human body, as well as mechanisms and rates of release from the body in the breath or by other excretory means.

Electronic aroma detection (EAD) technologies encompass a wide array of electronic-nose (e-nose)-type technologies with many different gas-detection mechanisms and operating principles. The many types of e-nose instruments range from surface acoustic wave (SAW), quartz crystal microbalance (QMB), metal oxide semiconducting (MOS) and conducting polymers (CP), to the newer DNA-carbon nanotubes, and many others that may be employed in sensors used in devices and systems of the invention.

As an example, it is known that exhaled breath contains biomarkers that point to presence of existing disease, including cancer. For example certain volatile organic compounds present in exhaled breath can be linked to certain diseases. Researchers at Technion—Israel Institute of Technology and Carmel Medical Center in Haifa, Israel have developed tiny flexible sensors that were used to test the breath of 43 volunteers that included 17 ovarian cancer patients, and they reported that their sensors achieved an 82% accuracy of detection.

The flexible sensors can be for example, made of gold nanoparticles that have molecules onto which volatile organic compounds (VOCs) attach to. When captured, the different VOCs bend the sensors at different angles depending on their nature and provide additional information as to the identity of the VOCs (thus informing more than simply whether a VOC was detected or not). Similarly, it has been reported that the presence of lung cancer could be diagnosed by a colorimetric sensor array to analyze exhaled breath. Mazzone, Peter J., Thorax 2007; 62; 565-568.

In certain embodiments, external devices/sensors (external meaning not on the microchip within the mouthpiece) can be integrated into the overall system of the invention to provide additional readings. For example, skin sensors can uses to monitor blood pressure. As another example, for EEG readings, sensors can be placed on the head and readings obtained that can wirelessly download the information into a receiving device (e.g. computer, laptop, smart phone, tablet, etc.) and the data can eventually be integrated with the data from the microchip to build complex biometric reports. See FIG. 16. As another example, blood pressure could be measured by an external device and the data could similarly be transmitted to a receiving device and integrated into the analysis and reports.

In some embodiments, disposable medical body area network (MBAN) sensor technology can be employed in the mouthpiece and external to the mouthpiece a part of systems of the invention.

With either sensors located on/in the mouthpiece or external sensors (not located on or in the mouthpiece) can be used to monitor and sense data points indirection. For example, sleep onset could be determined by monitoring changes in $O_2$ and $CO_2$ levels. As another example, core body temperature could be determined from labial skin temperature. Another example, would be to determine oxygen saturation from tidal $O_2$ instead of a skin-based measurement.

In another embodiment, the data from the external devices/sensors can wirelessly or wired send the data obtained from monitoring the patient to the cloud or other database and it may be matched with the incoming data from the mouthpiece and processed to form the reports. See FIG. 16.

From the data obtained by the sensors (as well as additional external devices/monitors, if included), multiple biomedical parameters used in sleep apnea diagnosis strategies can be calculated, including but not limited to, heart rate, heart rate variability, respiratory rate, wind speed, oxygen and carbon dioxide levels, snoring rate, pitch associated with snores, and airflow indirect quantification. In addition, data such as how long the user slept, and how many times the user was restless or woke up may also be measured. Further, there has been some data reported that suggests a relationship between symptomatic obstructive sleep apnea (OSA) and Gastroesophageal reflux disease (GERD). The prevalence of GERD has been shown about 58-62% of patients with OSA. See Green B T, et al., "Marked improvement in nocturnal gastroesophageal reflux in a large cohort of patients with obstructive sleep apnea treated with continuous positive airway pressure," Arch Intern Med. 2003; 163:41-45 and Herr J., "Chronic cough, sleep apnea, and gastroesophageal reflux disease," Chest. 2001; 120:1036-1037.

Accordingly, it may be desirable to be able to measure the pH of saliva to determine if the user is experiences any GERD symptoms.

In certain embodiments, the mouthpiece can be coated with electrically conductive nanotubules to capture electrical signals.

The mouth piece is not only useful in therapeutic purposes, e.g. treat sleep apnea, but can also be used for diagnostic purposes System The present invention also provides a system that allows, among other things, remote provide remote digital monitoring and remote data analysis. In addition to the mouthpiece, the system may be a nasal cannula and/or may be ear piece (e.g. ear buds) that can provide noise cancelling and also can be configured to transmit messages to the user from other components in the system. For example, messages could be relayed to the user via the earpiece to issue alerts if the system determines the user is sleeping on their back. As another example, alerts could be relayed to the user via the earpiece that are generated from the automated emergency alert system or even weather emergencies broadcasted for the area where the user is located. In another example alerts could be sent to the user via the earpiece to indicate that the devices or system are not functioning properly.

Figure 16:
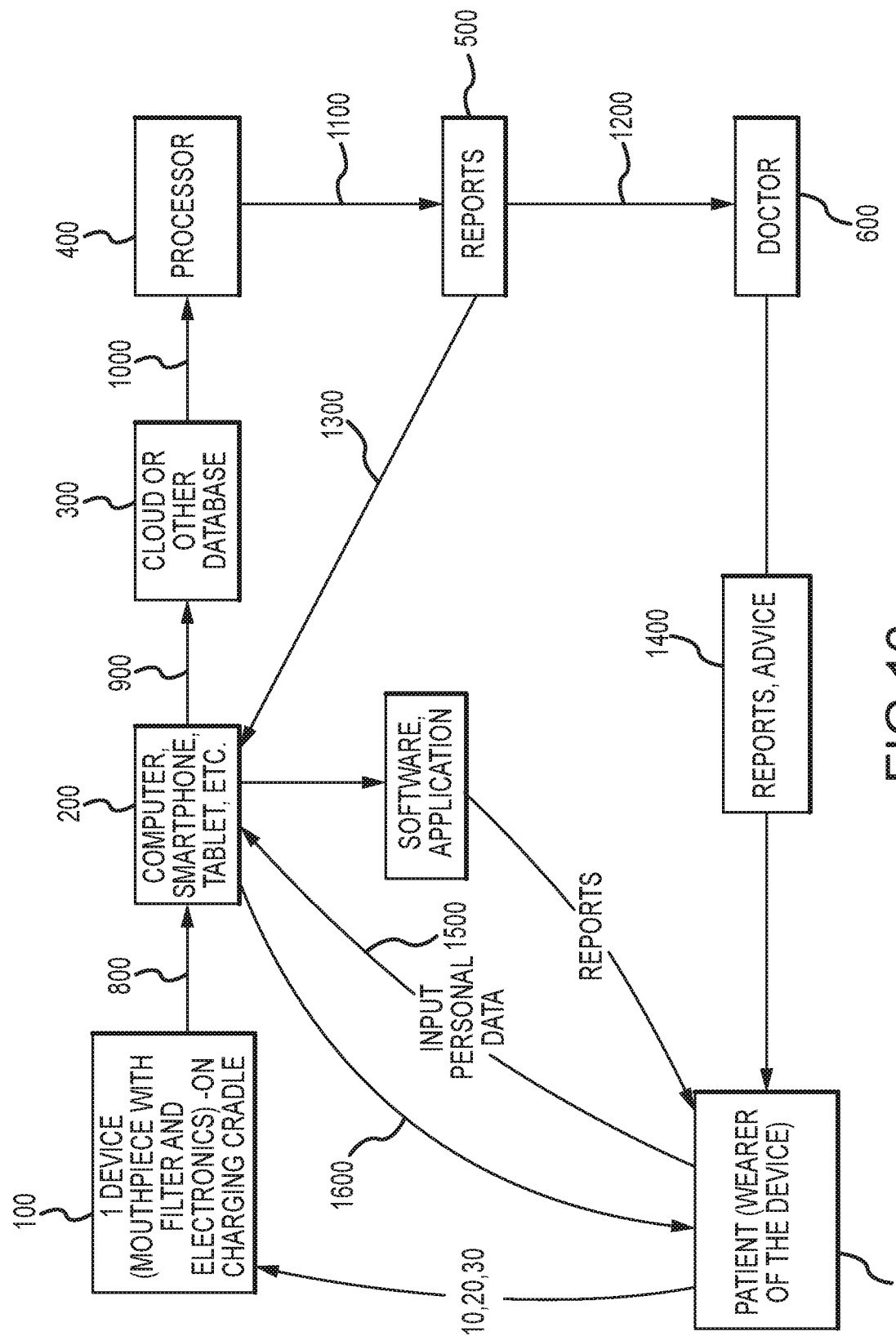
FIG. 16 provides an overview of a system of the invention.
Figure 17:
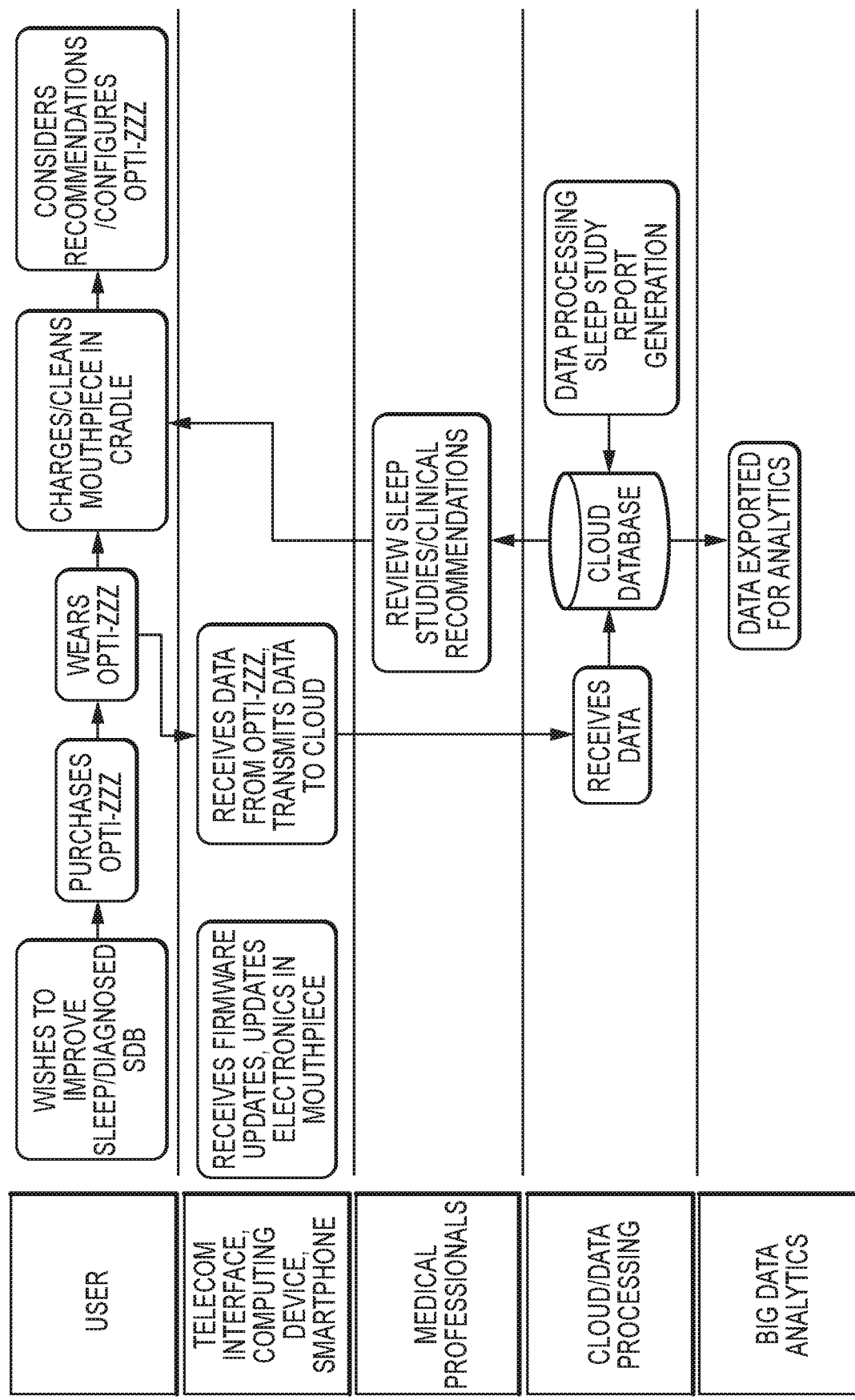
FIG. 17 provides an overview of a system of the invention.

Referring to FIG. 16, a depiction of one embodiment of the system is shown. The patient or user (wearer of the device) is shown as box 700. The user purchases and registers the device (110). After the user wears the device, the user places it on the charging cradle 50. Information (800) obtained from the sensors and saved onto the flash memory of the device is downloaded (depicted by arrow 800) to a receiving unit (200), which may be a computer, smart phone, tablet, etc. The figure shows the information being sent to the receiving unit while the device is on the charging cradle, but in some embodiments the data can be sent to the receiving unit intermittently or constantly while the user is wearing the device. The information (800) can be transmitted wirelessly or wired. The receiving unit (200) then transfers the data (900) associated with the IP address of the device to the cloud or any other database (300). The information is processed (1000) by a processing unit (400) to generate (1100) a report (500). In another embodiment, the receiving unit has a software program or an application that can process the information and generate the reports.

In certain embodiments, devices/sensors that are not on the microchip and the data obtained from these devices/sensors can be integrated into the overall system of the invention to provide additional readings. As shown in FIG. 16, external devices can obtain data obtained from the monitoring various parameters of the patient and can wirelessly download the information 800 into a receiving device 200 (e.g. computer, laptop, smart phone, tablet, etc.) and the data can eventually be integrated with the data from the microchip to build complex biometric reports.

In another embodiment, the data from the external devices/sensors can wirelessly or wired send the data 900 obtained from monitoring the patient to the cloud or other database 300 and it matched with the incoming data from the mouthpiece and processed 1100 to form reports 500. See FIG. 16.

Exemplary reports that can be generated, but are not limited to, reports such as standard sleep study reports (polysomnograms), health alerts, summary reports, reminders, or health tips, etc. Reports can also include information about the device. For example, but not limited to, such information can include reports noting if the device is not functioning properly or is functioning properly, needs a new battery, sensors are not working, availability of upgrades to software, sensors, etc. Reports can also inform the wearer that a different resistance filter grid insert should be used based on the reports.

The reports can be sent (1200) to a doctor (600) or can also be sent directly (1300) back to the receiving unit (200). The receiving unit (200) can send reports/alerts (1600) to the patient (700).

The patient (700) can then update the device with new electronics, or perhaps change to a different filter grid insert and/or a different filter flap.

The patient can also enter personal data and observations (1500) regarding the device, length of hours spent in bed, observations of sleep quality, age, height, weight, general health information etc. This data can be used in conjunction with the data obtained by the device of the invention and/or external sensors for generating reports.

In other embodiments, the doctor can use information received from multiple users' data stored on the cloud and processed for various studies and diagnosis trends. For example, the doctor may see that certain sections of the population who share certain common characteristics may all require a certain filter grid/filter flap configuration and can use this information to better calculate an optimal correct grid/flap configuration at the beginning of a new user's treatment.

Systems of the invention may comprise processes that titrate the mouthpiece to incorporate validation/feedback from a physician, patient acceptance/confirmation, or provide full automation. For example, electronics built into the mouthpiece could be used to maintain certain output levels based on feedback from the sensors. An algorithm may comprise input parameters that can be specified by a doctor or adjusted per the patient's personal preference.

Nasal Splint

Figure 18A:
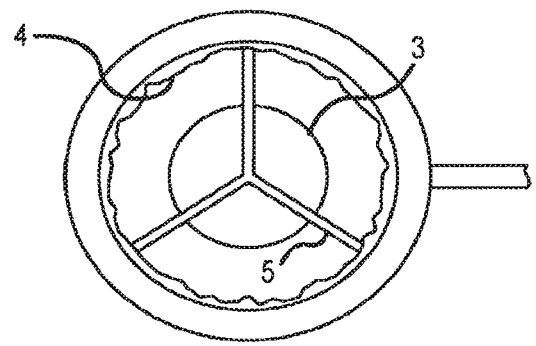
FIG. 18a provides a top view.
Figure 18B:
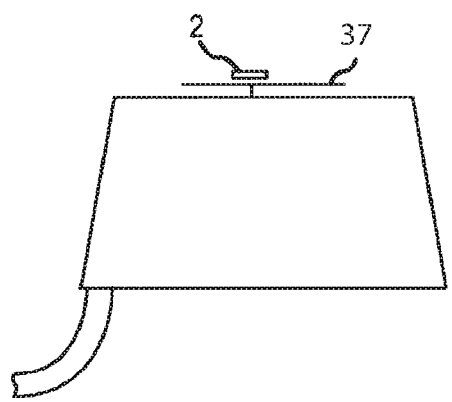
FIG. 18B provides a side view.
Figure 18C:
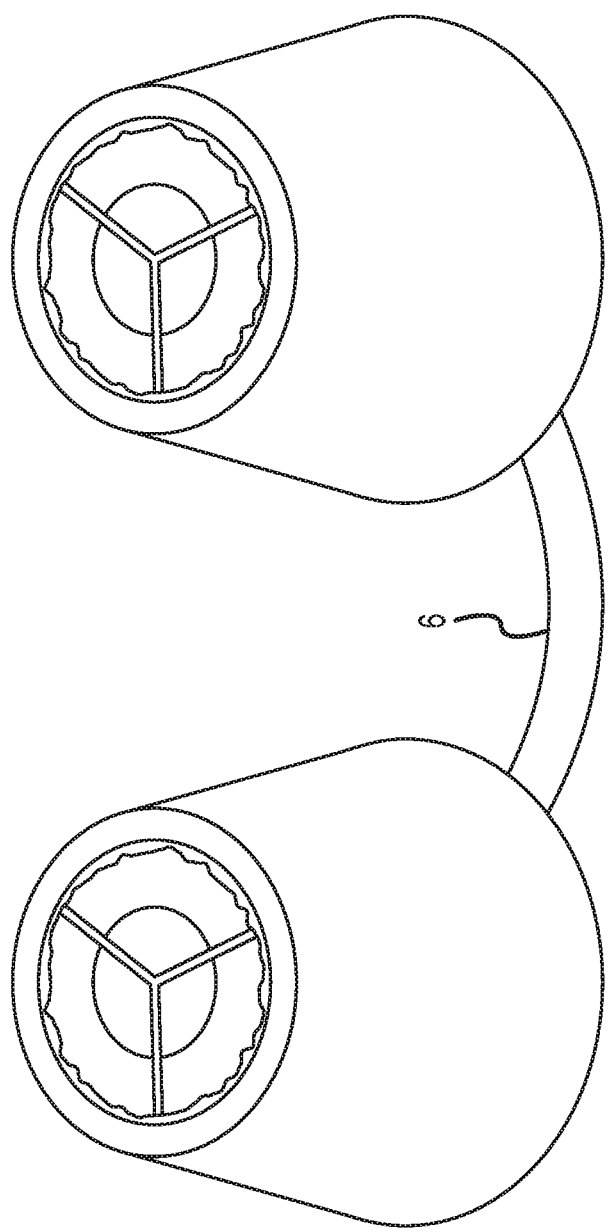
FIG. 18C provides an orthogonal view.

In some embodiments the device is a nasal splint having two nasal inserts. FIG. 18 provides an exemplary depiction. The splint works in the system similar to the mouthpiece in that they both have a filter assembly by which exhaling resistance is controlled. FIG. 18 shows a filter flap (37) that is used to adjust expiratory respiratory resistance. The filter flap is free to move above the nasal insert when the user inhales. When the user exhales, the filter flap is pushed against the nasal insert. The filter assembly has a fastener (2) for attaching the filter flap to the nasal insert. (3) provides the top view of filter flap. The nasal insert has a ring insert (4) for adjusting inspiratory resistance. There is provided a structure (5) for supporting the filter flap. A bridge (6) is provided for holding the two nasal inserts together.

Kits

The present invention provides kits. The kit preferably contains a mouthpiece, a filter assembly, various "resistance" filter grid inserts and different filter flaps, a re-charging cradle disinfecting cradle/cleaning system, instructions for use and product registration. The kit may have software that can be installed on a receiving unit in which to interact with data received from the device. The software may create the reports.

The kit may have a nasal splint, a filter assembly, various "resistance" filter grid inserts and different filter flaps, a re-charging cradle disinfecting cradle/cleaning system, instructions for use and product registration. The kit may have software that can be installed on a receiving unit in which to interact with data received from the device. The software may create the reports.

Methods of Treatment

The filter assembly placed within the protuberance 4 of the mouthpiece of the device optimizes or substantially optimizes esophageal pressure by creating an amount of aerodynamic drag in the protuberance/filter assembly. Esophageal pressure is created naturally by the sinuses when a user breathes through their nose. The sinuses increase air resistance by roughly 50%. Esophageal air pressure causes the sinuses to release Nitric Oxide (NO). The amount of NO released by the sinuses increases with the amount of esophageal pressure. NO is a bronchodilator, anti-bacterial, and vasodilator. NO and CO2 create complementary health effects.

Optimal CO2 causes the muscles around the airway to relax. Optimal CO2 also causes the smooth muscles around blood vessels to relax. Decreased CO2 can also cause the airway to constrict.

The filter grid insert and/or flap or combination thereof creates resistance in the airway that artificially limits the amount of air that can flow in either direction (inhale/exhale). This reduces the amount of carbon dioxide that is exhaled. This in turn causes the user to retain more carbon dioxide, thus helping the body to maintain optimum levels of carbon dioxide. Optimal carbon dioxide helps oxygenate the organs via the Bohr Effect (an increase in blood $CO_2$ concentration, which leads to a decrease in blood pH, will result in hemoglobin proteins releasing their load of oxygen). Further, optimal carbon dioxide helps the body regulate the impulse to breathe. When the carbon dioxide levels rise to a certain point, the body tells itself to breathe.

The science behind treating sleep apnea with the device of the present invention is based on idea that over breathing causes deleterious effects that can be reduced when proper breathing is practiced. Many health issues, such as sleep apnea are associated with improper breathing, the most common of which are over breathing and mouth breathing. When breathing volume is normal and at healthy levels, there is optimal oxygenation of tissues and organs, including the brain. Numerous factors present in every day of the modern lifestyle such as stress, can produce an almost instinctual desire or believe that it is necessary to take big, deep breaths, or hyperventilation, which is reality are not needed and are in fact, over-breathing. Characteristics of over breathing include mouth breathing, upper chest breathing, sighing, noticeable breathing during rest, and taking large breaths prior to talking.

The body is set up to breathe through the nose under normal circumstances. Nitric oxide is present in the nose, so when one breathes through the nose, a small amount of nitric oxide is delivered into the lungs. Nitric oxide plays a significant role in homeostasis, or the maintaining of balance within your body. Nitric oxide is also a bronchodilator, an antibacterial agent that helps neutralize germs and bacteria and a vasodilator.

There appears to be a feedback loop associated with over-breathing, in that the heavier breathing volume that is coming into the lungs cause a disturbance of blood gasses, including the loss of carbon dioxide ($CO_2$). Although one breathes to get rid of excess $CO_2$, it is important to maintain a certain amount of $CO_2$ in the lungs. If too much carbon dioxide is expelled through over-breathing, smooth muscles surrounding the airways constrict. Dehydration of the inner walls of the airways also can occur. The combination of these factors causes the airways to constrict. In addition, carbon dioxide also helps to relax smooth muscles surrounding the blood vessels. Thus, over breathing can cause the blood vessels to also constrict, which in turn delivers less oxygen to the body. So over-breathing actually delivers less oxygen than normal breathing.

As the airway constricts, there is a natural reaction to breathe more intensely as a compensatory mechanism. However, this causes an even greater loss of carbon dioxide, and cooling of the airway causes it to close even more, further completing the negative feedback loop.

This feedback loop can be observed when a person takes five or six big breaths in and out of the mouth. Most people will begin to experience some light-headedness or dizziness. This is because the big breaths expel too much carbon dioxide from the lungs, which causes the blood vessels to constrict and hence cause the light-headedness. So, the heavier one breathes, the less oxygen that is actually delivered throughout the body due to lack of carbon dioxide, which causes the blood vessels to constrict.

In addition, Christian Bohr discovered in 1904 that for proper oxygenation to take place, the body needs the presence of carbon dioxide. Inappropriate/unnecessary heavy breathing causes the loss of $CO_2$, which not only causes the blood vessels to constrict, but it also causes a greater affinity of the red blood cells with oxygen.

Accordingly, the device of the present invention, forces the wearer to breathe more appropriately (does not over-breathe) which in turn provides the correct amount of oxygenation to the body. Thus the wearer does not wake up gasping for breathes of air, because the wearer has taken in the appropriate/necessary amount of oxygen.

Methods of the invention may utilize nasal splints described herein. In certain embodiments both the mouthpiece and the nasal splints are used together.

Methods of Monitoring

The present invention provides methods of monitoring patient compliance with wearing devices (including the mouthpiece and the nasal splint) of the invention. For example, the device can measure the number of hours the patient wears the device each night and likewise, if no data is generated for a certain night or number of nights, the reports can note noncompliance for that night's sleep to the physician.

The present invention also provides a method of diagnosing sleep apnea. The data obtained from the microchip and/or external devices is analyzed and based on the biometrics, it can be determined whether the user suffers from sleep apnea.

Since the data from the device of the invention is analyzed by software or applications in the processor (or in certain embodiments the receiving devices), it can determine whether the device is operating in within the desired tolerances or parameters.

Systems of the present invention can be used to monitor and report to the user/physician how effectively the device is at reducing snoring, stress, hyperventilation, airway obstruction, and/or whether the patient has positioned their soft palate in a way that stops them from breathing through their mouth. The device directs air through their nasal airway. The device/system can detect whether the user is breathing through their mouth. A separate nasal cannula may be used to determine whether the user was breathing through their nose, or a combination of nose and mouth. Further, the system can generate in the reports, guidance as to use of a different filter grid insert/filter flap combination depending upon the data obtained from previous readings.

The system of the present invention can also be used to monitor nocturia—waking up repeatedly during the night to urinate, which could be useful for diagnosis other non-sleep related disorders (such as enlarged prostrate or cardiovascular stress). The device and system can be used to detect the user getting up and walking around. Data can be analyzed for changes related to waking up, getting up and then going back to sleep. Actigraphy may indicate what the person was doing, or the level/type of physiological tension that led to the person getting out of bed.

In addition, the reports/data can be saved and compared to measure changes in biometrics over time as an indicator of health changes. Specific patterns can be monitored across populations and used treat demographic and other trends. For example, if people who live close to trains start snoring when they hear the train horn, the system can generate a suggestion for all people who live close to train tracks. Another example could be a trend towards heart disease in urban areas. If the cause happened to be population density, or higher crime rates, specific relaxation therapy or lifestyle changes could be suggested to help manage the stress. The suggestions could be presented along with personal and mass data trends and expert opinions on the topic.

In addition, the system can be used to measure changes in stress that impact sleep. For example, if the patient records that he is experiencing higher levels of stress, the system can track these user input data with the biometric data obtained from the sensors and can correlate or track how the increased stress affects the patient's sleep. Similarly, if the patient records that he started yoga and other exercise, the device can correlate or track how these activities affects (most likely improves) the patient's sleep.

As a another non-limiting example, the system can track and record the time the patient went to bed and the number of hours in bed (wearing the device) and the system can compare and correlate the data to determine if certain late or early bedtimes and/or wake up times effects the patients sleep. For example, the patient may find out that 8 hours of sleep from the hours of 11:00 pm-7 am provide a much better quality of sleep than the hours of 1 am-9 am.

The invention claimed is:

1. A system for treating sleep apnea in a patient, the system comprising:
   a mouthpiece;
   a bi-directional filter assembly; and
   a microchip comprising sensors,
   wherein the filter assembly and the microchip are positioned within the mouthpiece, and
   wherein the filter assembly comprises:
   a filter grid;
   a removable filter grid insert restrained by a slot of the filter assembly behind the filter grid, wherein the filter assembly is configured to bi-directionally direct a first portion of air through the filter grid insert and a second portion of air around the filter grid insert through a portion of the filter grid adjacent to the filter grid insert; and
   a filter flap that is configured to be closed against the filter grid insert during the patient's exhalation to create greater resistance during the patient's exhalation than inhalation to treat sleep apnea.

2. The system of claim 1, further comprising:
   a recharging cradle; and
   a non-transitory computer readable storage medium including instructions that, when executed by a processor, cause the system to analyze data obtained from the sensors and to generate reports.

3. The system of claim 1, further comprising a hydrating mesh surrounding the filter assembly.

4. The system of claim 1, wherein the slot of the filter assembly is positioned at a region of the filter assembly proximal to the patient's teeth.

5. The system of claim 1, wherein the slot of the filter assembly is positioned at a region of the filter assembly furthest away from the patient's teeth.

6. The system of claim 1, wherein the filter grid insert comprises a plurality of tubes with protuberances for generating laminar air resistance.

7. The system of claim 1, further comprising:
   a second removable filter grid insert configured to be placed in the slot of the filter assembly, replacing the removable filter grid insert restrained by the slot of the filter assembly.

8. The system of claim 1, further comprising:
   a face plate for the filter grid being positioned on a side of the [system] closer to the patient's mouth, wherein the filter flap is attached to the face plate.

9. The system of claim 8, wherein the filter flap is configured to be removable from the face plate and replaced with a different filter flap.

10. A device for treating sleep apnea in a patient, the device comprising:
    a mouthpiece;
    a bi-directional filter assembly positioned within the mouthpiece comprising:
    a filter grid;
    a face plate for the filter grid, the face plate being positioned on a side of the device closer to the patient's mouth;
    a removable filter grid insert restrained by a slot near the face plate, wherein the filter assembly is configured to bi-directionally direct a first portion of air through the filter grid insert and a second portion of air around the filter grid insert through a portion of the filter grid adjacent to the filter grid insert, wherein the filter grid insert comprises a plurality of tubes with protuberances for generating laminar air resistance; and
    a removable filter flap restrained by the faceplate to create a greater resistance during the patient's exhalation than inhalation;
    a hydrating mesh surrounding the filter assembly; and
    a microchip comprising sensors positioned within the mouthpiece.

11. A method for configuring a device for treating sleep apnea in a patient, the method comprising:
    determining, using a microchip and sensors positioned within a mouthpiece of the device, a measure of lung performance of the patient while using the device with a first removable filter grid insert, wherein the first removable filter grid insert is restrained by a slot of a filter assembly, wherein the filter assembly is configured to direct a first portion of air through the slot of the filter assembly and a second portion of air around the slot of the filter assembly;
    determining a second removable filter grid insert for use with the device based on the measure of lung performance; and
    indicating that the first removable filter grid insert should be replaced by the second removable filter grid insert in the device.

* * * * *